United States Patent
Longo et al.

(10) Patent No.: US 11,719,668 B2
(45) Date of Patent: Aug. 8, 2023

(54) FUNCTIONALIZED FIELD-EFFECT TRANSISTOR COMPRISING A MOLECULARLY IMPRINTED POLYMER OR A PROBE MATERIAL FOR SENSING BIOMARKERS

(71) Applicant: Xsensio SA, Lausanne (CH)

(72) Inventors: Johan Frédéric Longo, Yverdon-les-Bains (CH); Neil Ebejer, Lausanne (CH); Hoël Maxime Guérin, Lausanne (CH); Fabien Patrick Wildhaber, Troistorrents (CH)

(73) Assignee: Xsensio SA, Lausanne (CH)

( * ) Notice: Subject to any disclaimer, the term of this patent is extended or adjusted under 35 U.S.C. 154(b) by 288 days.

(21) Appl. No.: 16/975,692

(22) PCT Filed: Mar. 6, 2019

(86) PCT No.: PCT/EP2019/055613
§ 371 (c)(1),
(2) Date: Aug. 25, 2020

(87) PCT Pub. No.: WO2019/170775
PCT Pub. Date: Sep. 12, 2019

(65) Prior Publication Data
US 2021/0364466 A1 Nov. 25, 2021

Related U.S. Application Data

(60) Provisional application No. 62/656,882, filed on Apr. 12, 2018, provisional application No. 62/639,449, filed on Mar. 6, 2018.

(51) Int. Cl.
*G01N 27/414* (2006.01)
*A61B 5/145* (2006.01)
(Continued)

(52) U.S. Cl.
CPC ..... *G01N 27/4145* (2013.01); *G01N 27/4146* (2013.01); *G01N 27/4148* (2013.01);
(Continued)

(58) Field of Classification Search
None
See application file for complete search history.

(56) References Cited

U.S. PATENT DOCUMENTS 6,616,823 B2   9/2003   Kopf-Sill
9,116,145 B2   8/2015   Li et al.
(Continued)

FOREIGN PATENT DOCUMENTS

JP   2008/082988 A   4/2008
WO   WO-2010/045247 A1   4/2010
(Continued)

OTHER PUBLICATIONS

Z. Iskierko, et al., "Extended-gate field-effect transistor (EG-FET) with molecularly imprinted polymer (MIP) film for selective inosine determination", Biosensor and Bioelectronics, 74, p. 526-533 + Supplemental p. 1-8, Dec. 15 (Year: 2015).*
(Continued)

*Primary Examiner* — J. Christopher Ball
(74) *Attorney, Agent, or Firm* — Choate, Hall & Stewart LLP; William R. Haulbrook; Michael D. Schmitt

(57) ABSTRACT

Presented herein are systems, methods, and architectures related to functionalization of the metallic gates of field-effect transistors (FETs) and the use of the functionalized FETs as biochemical sensors in liquid samples. The functionalization can either be a molecularly imprinted polymer or a probe material. The functionalized FETs can be used in devices for analyte detection/quantification. In particular,
(Continued)

the functionalized FETs are used in devices for the detection and/or quantification of cytokines (e.g. interleukin) and/or cholesterol (LDL or HDL).

17 Claims, 12 Drawing Sheets

Specification includes a Sequence Listing.

(51) Int. Cl.
    *A61B 5/00*         (2006.01)
    *G01N 33/487*     (2006.01)

(52) U.S. Cl.
    CPC ......... *A61B 5/14517* (2013.01); *A61B 5/4266* (2013.01); *G01N 33/48707* (2013.01)

(56) References Cited

U.S. PATENT DOCUMENTS

| | | |
|---|---|---|
| 9,810,660 B2 | 11/2017 | Hu et al. |
| 10,653,342 B2 | 5/2020 | Rogers et al. |
| 10,925,523 B2 | 2/2021 | Rogers et al. |
| 2002/0049389 A1 | 4/2002 | Abreu |
| 2004/0129678 A1 | 7/2004 | Crowley et al. |
| 2007/0027383 A1 | 2/2007 | Peyser et al. |
| 2010/0147683 A1 | 6/2010 | Vanaja et al. |
| 2013/0291627 A1 | 11/2013 | Hu et al. |
| 2016/0310049 A1 | 10/2016 | Rowe et al. |
| 2017/0100102 A1 | 4/2017 | Heikenfeld |
| 2017/0231571 A1 | 8/2017 | Rogers et al. |
| 2018/0020966 A1 | 1/2018 | Begtrup et al. |
| 2018/0064377 A1 | 3/2018 | Rogers et al. |
| 2018/0153451 A1 | 6/2018 | Heikenfeld et al. |
| 2018/0199866 A1 | 7/2018 | Heikenfeld |
| 2019/0049405 A1 | 2/2019 | Kajisa et al. |
| 2019/0110722 A1* | 4/2019 | Ionescu .............. A61B 5/14517 |
| 2019/0183398 A1 | 6/2019 | Heikenfeld et al. |
| 2019/0191998 A1 | 6/2019 | Heikenfeld et al. |
| 2019/0191999 A1 | 6/2019 | Heikenfeld et al. |
| 2019/0192000 A1 | 6/2019 | Heikenfeld et al. |
| 2020/0077988 A1 | 3/2020 | Heikenfeld |
| 2020/0315503 A1 | 10/2020 | Heikenfeld et al. |

FOREIGN PATENT DOCUMENTS

| | | | |
|---|---|---|---|
| WO | WO-2012/050873 A2 | 4/2012 | |
| WO | WO-2016/030869 A1 | 3/2016 | |
| WO | WO-2017/019573 A1 | 2/2017 | |
| WO | WO-2017/163715 A1 | 9/2017 | |
| WO | WO-2018/047125 A1 | 3/2018 | |
| WO | WO-2018047125 A1 * | 3/2018 | ......... A61B 10/0045 |
| WO | WO-2018/223090 A1 | 12/2018 | |
| WO | WO-2019/060689 A1 | 3/2019 | |
| WO | WO-2019/170775 A1 | 9/2019 | |
| WO | WO-2019/170776 A1 | 9/2019 | |
| WO | WO-2021/099610 A1 | 5/2021 | |

OTHER PUBLICATIONS

Betatache, A., et al., Gold electrodes modified with molecular imprinted acrylate polymer for impedimetric determination of testosterone, Sensors & Transducers Journal, 27(Special Issue):92-99, (2014).

Craighead, H., Future lab-on-a-chip technologies for interrogating individual molecules, Nature, (Jul. 27, 2006), 442:387-393, (2006).

Diacci, C. et al., Label-free detection of interleukin-6 using electrolyte gated organic field effect transistors, Biointerphaases, 12(5):05F401-1-05F401-6, (2017).

Gao, W. et al., A. Javey, Fully integrated wearable sensor arrays for multiplexed in situ perspiration analysis, Nature, 529(7587):509-514, (2016).

Heikenfeld, J., Non-invasive Analyte Access and Sensing through Eccrine Sweat: Challenges and Outlook circa, , 28(6):1242-1249, (2016).

International Search Report, International Application No. PCT/EP2019/055613 (Functionalized Field-Effect Transistor Comprising a Molecularly Imprinted Polymer or a Probe Material for Sensing Biomarkers, filed Mar. 6, 2019), issued by ISA/European Patent Office, 6 pages, Jun. 19, 2019.

Iskierko, Z. et al., Molecularly imprinted polymer based extended-gate filed-effect transistor chemosensors for phenylalanine enantioselective sensing, Journals of Matierls Chemistry C, 5(4):969-977, (2016).

Morak; Jurgen et al., Design and evaluation of a telemonitoring concept based on NFC-enabled mobile phones and sensor devices, IEEE transactions on information technology in biomedicine, (20120000), 16.1:17-23.

Tang, P. et al., An electrochemical sensor based on iron (II, III)@graphene oxide@molecuraly imprinted polymer nanoparticles for interleukin-8 detection in saliva, Analytical Methods, 7(18):7784-7791, (2015).

Written Opinion, International Application No. PCT/EP2019/055613 (Functionalized Field-Effect Transistor Comprising a Molecularly Imprinted Polymer or a Probe Material for Sensing Biomarkers, filed Mar. 6, 2019), issued by ISA/European Patent Office, 13 pages, dated Jun. 19, 2019.

Xiao, Y. et al., Preparation of electrode-immobilized, redox-modified oligonucleotides for electrochemical DNA and aptamer-based sensing, Nature Protocols, 2(11):2875-2880, (2007).

Bellando, F. et al., Lab on skin™: 3D monolithically integrated zero-energy micro/nanofludics and FD SOI ion sensitive FETs for wearable multi-sensing sweat applications, IEEE International Electron Devices Meeting (IEDM), 4 pages, (2017).

* cited by examiner

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1
tctgtctcga ggggtagctg                                          20

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2
caatgtctca ccaagctctg                                          20

<210> SEQ ID NO 3
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 3
acctcgattt tatattattt cgcttaccaa caactgcaga                    40
```

FUNCTIONALIZED FIELD-EFFECT TRANSISTOR COMPRISING A MOLECULARLY IMPRINTED POLYMER OR A PROBE MATERIAL FOR SENSING BIOMARKERS

CROSS-REFERENCE TO RELATED APPLICATIONS

This application is a national stage entry under 35 U.S.C. § 371 of PCT/EP19/55613, filed on Mar. 6, 2019, which claims priority to and the benefit of U.S. Provisional Patent Application No. 62/639,449, filed Mar. 6, 2018, and U.S. Provisional Patent Application No. 62/656,882, filed Apr. 12, 2018, the contents of which are incorporated by reference herein in their entirety.

FIELD OF THE INVENTION

This invention relates generally to methods, systems, and architectures for analyzing biomarkers in biofluids or in mixtures comprising a biofluid. In particular, in certain embodiments, this invention relates to functionalized field-effect transistors for the detection and/or quantification of cytokines and/or cholesterol in a biofluid.

BACKGROUND OF THE INVENTION

Cytokines are proteins that are similar to hormones, which are produced by cells in response to various stimuli (e.g., involved in cell signaling). Their release affects the behavior of cells around them. Cytokines are involved in autocrine, paracrine, and endocrine signaling and act as immunomodulation agents. There are hundreds of cytokines that are classified according to their structure. Classes of cytokines include chemokines, interferons, interleukins, lymphokines, and tumor necrosis factors. Cytokines are produced by a broad range of cells, including immune cells, and a given cytokine may be produced by more than one type of cell. Cytokines have a significant role in the immune system, specifically in host response to infection, immune responses, inflammation, trauma, sepsis, cancer, and reproduction.

Existing methods that are used to determine the concentration of cytokines in a biofluid sample include enzyme-linked immunosorbent assay (ELISA), enzyme-linked immune absorbent spot (ELISPOT), antibody arrays, bead-based assays. These existing methods for measuring cytokine concentration have a high cost, are complicated to perform, and require long testing times and relatively large sample volumes. Additionally, none of these existing methods accommodate long-term or continuous monitoring of cytokines, and existing cytokine measurement techniques are affected by changes in measurement conditions (e.g., temperature, pH, ionic strength) and storage conditions. The materials used for these measurements also have a short shelf life and are single-use (e.g., the same test cannot be reused).

Cholesterol, which is also known as cholesterin or cholesteryl alcohol, is an organic molecule with a molar mass of 385 g/mol.

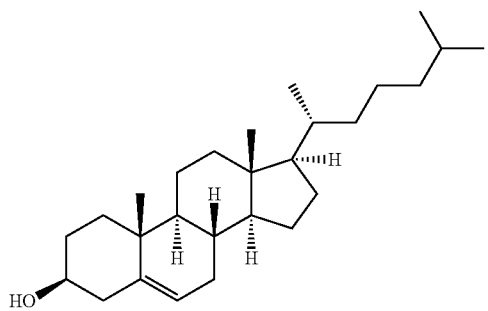

It is a sterol and a precursor of steroid hormones. Cholesterol is a type of lipid molecule that is synthesized by human/animal cells and plays an important role as a structural component of human and animal cell membranes.

Lipoproteins are particulate complexes that transport cholesterol and other lipids through extracellular fluid, which includes blood and blood plasma. Lipoproteins are classified into groups according to their density. Generally, large lipoprotein particles have a low density, and small lipoprotein particles have a higher density. Examples of the different classes of lipoproteins include chylomicrons, very low-density lipoprotein (VLDL), low-density lipoprotein (LDL), intermediate-density lipoprotein (IDL), and high-density lipoprotein (HDL).

There is a need for improved methods and apparatus for detecting cytokines, cholesterol, and lipoproteins.

SUMMARY OF THE INVENTION

Presented herein are apparatus, systems, methods, and architectures related to functionalization of the metallic gates (e.g., or the extended metallic gates) of field-effect transistors (FETs) and the use of the functionalized FETs as biochemical sensors in liquid samples. For example, in certain embodiments, the functionalized FETs are used in devices for analyte detection/quantification (e.g., on-skin detection of analytes in a biofluid, e.g., sweat). In particular, the functionalized FETs are used in apparatus for the detection and/or quantification of cytokines, cholesterol and/or lipoproteins.

In certain embodiments, the present disclosure relates to (i) molecularly imprinted polymer (MIP) membranes prepared via electro-polymerization, (ii) MIP membranes prepared via photo-polymerization, (iii) MIP membranes prepared via deposition (e.g., drop casting), (iv) MIP membranes prepared via polymerization, (v) aptamer immobilization, and (vi) protein immobilization. For example, any one or more of (i) through (vi) may be disposed on the surface of a metallic gate or extended metallic gate of a field-effect transistor, thereby enabling highly selective detection of specific analytes (e.g., analytes in solutions that come into contact with the membranes). In certain embodiments, any one or more of (i) through (vi) can be disposed on the surface of an electrode for the selective detection of specific analytes via electrochemical analysis techniques (e.g., amperometry, potentiometry). Other embodiments include methods related to the creation of any one or more of (i) through (vi) above.

Using the compositions, apparatus, and methods described herein cytokines and/or lipoproteins can be monitored in a variety of biofluids such as, for example, tears, saliva or sweat for non-invasive diagnosis in addition to the analysis of blood, blood plasma, extracellular fluid, urine, and the like.

The use of FET sensors enables the accurate detection of molecules of interest (e.g., cytokines, e.g., lipoproteins) that are present at a low concentration in a biofluid. The ability to detect a low concentration of a molecule of interest can be essential for early disease diagnosis. For example, interleukin 6 (IL-6) circulates in the body at a typical concentration of $10^{-12}$ M (e.g., in the picomolar concentration range). In certain embodiments, the apparatus and methods described herein can be used to measure cytokines in a biofluid at a concentration of about one picomolar ($10^{-12}$ M) or greater. In some embodiments, the apparatus and methods described herein can be used to measure cytokines in a biofluid at a concentration of about one femtomolar ($10^{-15}$ M) or greater. FET sensors provide signal amplification and a high surface area-to-volume ratio. These features contribute to the ability of the apparatus described herein to detect and/or measure molecules of interest at low concentrations.

Moreover, the compositions described herein (e.g., molecularly imprinted polymers and probe-functionalized materials), when coupled with FET or electrode sensors, allow for device miniaturization. Because of this miniaturization, each sensor requires only a very small volume of biofluid for each measurement (e.g., about 1 nL or less). These small sample volumes can be collected non-invasively and with minimal or no discomfort to a person whose biofluid is being analyzed. The devices and apparatus also have a low energy consumption (e.g., about 100 nW or less) and can be easily transported or included in wearable, on-body biosensors. Additionally, the miniaturized and reversible biosensors described herein can be used for on-body measurements of biofluids.

The compositions and apparatus described herein exhibit less degradation (e.g., they have an improved stability) over time and a longer shelf-life than existing assays used to measure similar molecules of interest (e.g., the same or other cytokines and lipoproteins as those described herein). The compositions and apparatus described herein can also function over a broader range of operating conditions (e.g. of pH, temperature, ionic strength, and the like) than existing tools used to measure these analytes. Methods are also described herein for re-using the devices and apparatus described herein such that continuous monitoring and long term measurements are possible.

In one aspect, the present disclosure is directed to an apparatus for detecting and/or monitoring one or more molecules of interest in a biofluid, the apparatus comprising: a field-effect transistor disposed on and/or within a substrate (e.g., a substrate conformable to human skin), the field-effect transistor comprising one or more gates (e.g., an extended metallic gate, e.g., a gate dielectric without a metallic gate); and one or more compositions for selectively sensing (e.g., detecting and/or quantifying) at least one of the one or more molecules of interest, wherein: the one or more compositions comprise a molecularly imprinted polymer (MIP) membrane and/or one or more probe materials, and each of the one or more compositions is disposed on (e.g., fully or partially covering) at least a portion of a surface of at least one of the one or more metallic gates [e.g., thereby enabling detection of a specific analyte (e.g., an analyte in solution that comes into contact with the one or more composition), e.g., one or more cytokines, e.g., one or more lipoproteins (e.g., cholesterol)].

In certain embodiments, the one or more molecules of interest comprise one or more members selected from the group consisting of cytokines (e.g., IL-6, e.g., IL-10), cholesterol, and lipoproteins [e.g., chylomicron, e.g., very low-density lipoprotein (VLDL), e.g., low-density lipoprotein (LDL), e.g., intermediate-density lipoprotein (IDL), e.g., high-density lipoprotein (HDL)].

In certain embodiments, the biofluid comprises a member selected from the group consisting of sweat, tears, saliva, urine, blood, blood plasma, and extracellular fluid. In certain embodiments, the biofluid is sweat.

In certain embodiments, the field-effect transistor is a fully depleted field-effect transistor (e.g., as described in U.S. patent application Ser. No. 15/913,714 filed Mar. 6, 2018) or a Fin FET (e.g., as described in European Patent Application No. 16188227.9 filed Sep. 10, 2016 and U.S. patent application Ser. No. 15/453,920 filed Mar. 9, 2017). In certain embodiments, at least one of the one or more metallic gates is an extended metallic gate.

In certain embodiments, at least one of the one or more compositions comprises the molecularly imprinted polymer (MIP) membrane, wherein the molecularly imprinted polymer membrane comprises a plurality of cavities (e.g., adsorption sites) that are shaped and sized to selectively bind to one or more molecules of interest (e.g., target analyte(s)). In certain embodiments, the molecularly imprinted polymer (MIP) membrane has a thickness in a range from 1 nm to about 100 µm. In certain embodiments, the molecularly imprinted polymer (MIP) membrane comprises one or more materials selected from the group consisting of for example polyvinyl chloride, polystyrene, and poly-(3-aminophenylboronic acid) and derivative, polyaniline and derivative (such as p-Phenylenediamine), polysiloxane and derivative, polypyrrole, poly(3,4-ethylenedioxythiophene). In certain embodiments, the molecularly imprinted polymer (MIP) membrane is disposed on 50% or more of the surface of the at least one of the one or more metallic gates. In certain embodiments, the molecularly imprinted polymer is prepared via electro-polymerization, photo-polymerization, deposition (e.g., drop casting), or via polymerization.

In certain embodiments, at least one of the one or more compositions comprises the one or more probe materials, wherein the one or more probe materials comprise a chemical and/or a biological receptor (e.g., LDL-R, e.g., HDL-R) and/or an aptamer. In certain embodiments, the one or more probe materials comprise one or more members selected from the group consisting of: LDL-R, HDL-R, a DNA sequence, an RNA sequence, and a peptide sequence (e.g., wherein each of the one or more probe materials comprises a receptor or a protein or amino acid sequence that is complementary to a corresponding ligand or a corresponding protein or amino acid sequence of a corresponding molecule of interest of the one or more molecules of interest). In certain embodiments, the one or more probe materials comprise 5'-TCTGTCTCGAGGGGTAGCTG-3' (SEQ ID NO.1), 5'-CAATGTCTCACCAAGCTCTG-3' (SEQ ID NO.2), and/or 5'-ACCTCGATTTTATATTAT-TTCGCTTACCAACAACTGCAGA-3' (SEQ ID NO.3).

In certain embodiments, the apparatus comprises: an interface (e.g., and/or interface surface), the interface comprising at least one biocompatible material for contacting a body part (e.g., skin of a human); at least one inlet for receiving a biofluid; at least one outlet for evacuating the biofluid; and at least one microfluidic and/or nanofluidic channel in fluid communication with the at least one inlet, at least one of the one or more compositions disposed on the at least one of the one or more metallic gates of the field-effect transistor, and the at least one outlet.

In certain embodiments, the at least one microfluidic and/or nanofluidic channel has an internal volume in a range from about 0.1 nL to about 10 μL. In certain embodiments, the interface has an external surface area less than about 40 cm$^2$. In certain embodiments, the interface has an external surface area in a range from about 100 μm$^2$ to about 40 cm$^2$.

In certain embodiments, the apparatus further comprises an electronic circuit operably connected to the field-effect transistor, wherein produces and/or measures and/or transmits signals representative of measured data (e.g., a drain voltage, e.g., a drain current) from the field-effect transistor corresponding to a presence and/or amount of at least one of the one or more molecules of interest.

In certain embodiments, the apparatus comprises a wireless communication element for transmitting data and/or signals measured and/or calculated by the electronic circuit to an external device (e.g., a computing device, e.g., a mobile computing device).

In certain embodiments, the apparatus has a weight in a range from about 125 milligrams to about 1 gram.

In certain embodiments, the apparatus comprises a fixture module (e.g., one or more acrylate-based, biocompatible, and/or medical grade adhesives or tapes, e.g., one or more mechanically fastened straps) for disposing (e.g., affixing) the apparatus on a body part (e.g., skin of a wearer) [e.g., wherein the fixture module includes a temporary (e.g., reversible) adhesive, is water-resistant, and has an external surface area of about 40 cm$^2$ or less] (e.g., wherein the fixture module has an external surface area of about 5 cm$^2$ or less). In certain embodiments, the apparatus comprises a skin patch for disposing (e.g., affixing) the apparatus on a body part (e.g., skin of a wearer).

In certain embodiments, the apparatus comprises a reference electrode (e.g., a quasi-reference electrode, e.g., a Ag/AgCl quasi-reference electrode). In certain embodiments, the apparatus comprises a power supply (e.g., for applying a voltage or current to the field effect transistor).

In certain embodiments, a volume of the biofluid is about 10 microliters (A) or less. In certain embodiments, a power consumption of the device is about 100 nanowatts (nW) or less.

In certain embodiments, at least one of the one or more molecules of interest is a cytokine, and the cytokine is present in the biofluid at a concentration in a range from about 1 femtomolar ($10^{-15}$ M) to about 1 picomolar ($10^{-9}$ M).

In certain embodiments, at least one of the one or more molecules of interest is a lipoprotein (e.g., LDL, e.g., LDL-Ch, e.g., HDL, e.g., HDL-Ch), and the lipoprotein is present in the biofluid at a concentration in a range from about 1 nanomolar ($10^{-9}$M) to about 100 millimolar ($10^{-3}$ M).

In certain embodiments, the biofluid is not processed (e.g., to separate blood serum from blood plasma) prior to detecting and/or monitoring the one or more molecules of interest in the biofluid.

In certain embodiments, the one or more molecules of interest are detected and/or monitored in the biofluid continuously and/or for an extended period of time (e.g., days, weeks, or months).

In one aspect, the present disclosure is directed to a method of using the apparatus of any one of the preceding claims for detecting and/or monitoring the one or more molecules of interest in the biofluid, the method comprising contacting the device (e.g., an interface of the apparatus) to a surface (e.g., to a surface of a body part, e.g., to human skin) so that the biofluid (e.g., sweat) comes in contact with at least one of the one or more compositions and an electrical signal can be detected and/or monitored from the apparatus (e.g., a current or voltage measured at the field-effect transistor, e.g., a drain voltage, e.g., a drain current), wherein the electrical signal is indicative of a presence and/or a concentration of the one or more molecules of interest (e.g., wherein the method comprises overoxidizing the metallic gate of the FET to remove molecules of interest from the surface and prepare the apparatus for subsequent detection and/or monitoring).

In one aspect, the present disclosure is directed to a method of manufacturing a molecularly imprinted polymer membrane, the method comprising: contacting a template species with one or more monomers [e.g., one or more functional monomers (e.g., monomers comprising an amine group, a thiol group, and/or a carboxy group) and/or one or more structural monomers] (e.g., to produce a monomer-template complex); following contacting the template species with the one or more monomers, exposing the one or more monomers to a crosslinking agent and/or performing a crosslinking step for the one or more monomers (e.g., wherein the crosslinking step comprises an electro-polymerization step or a photo-polymerization step) to produce a polymer membrane, said polymer membrane comprising bound template species (e.g., template species covalently or non-covalently attached to the polymer membrane, e.g., template species embedded in the polymer membrane); and removing at least a portion of the bound template species from the polymer membrane [e.g., via proteinase digestion, e.g., via washing in a fluid (e.g., water, e.g., a solvent)] to produce the molecularly imprinted polymer membrane [e.g., wherein the molecularly imprinted polymer membrane comprises a plurality of cavities (e.g., adsorption sites) that are shaped and sized to selectively bind to a molecule of interest (e.g., wherein the molecule of interest is the template species)].

In certain embodiments, the one or more monomers comprises ethylene and/or propylene.

In certain embodiments, the template species comprise one or more molecules of interest [e.g., one or more target analytes, e.g., one or more cytokines (e.g., interleukin IL-6, interleukin IL-10), e.g., one or more lipoproteins (e.g., LDL, e.g., LDL-Ch, e.g., HDL, e.g., HDL-Ch)].

In certain embodiments, the step of contacting the template species with the one or more monomers is performed on or near a surface of a metallic gate (e.g., an extended metallic gate) of a field-effect transistor.

In certain embodiments, the one or more monomers comprise one or more members selected from the group consisting of: an electrochemically polymerizable monomer (e.g., aminophenyl boronic acid, phenyl boronic acid, acrylamide, aniline, pyrrole), a photocurable monomer (e.g., styrene, oligomeric acrylate), a chemically polymerizable monomer (e.g., 3-aminophenyl boronic acid, N-methacryloyl-(L)-tyrosine methyl ester, methacrylic acid).

In certain embodiments, the method includes the step of exposing the one or more monomers to a crosslinking agent [e.g., methylene bisacrylamide (MBA)] [e.g., and to a free radical source (e.g., ammonium persulfate), e.g., and to one or more salts and/or buffers] to produce a polymerizable mixture; and heating the polymerizable mixture (e.g., at 37° C. for 90 min) to produce the polymer membrane.

In certain embodiments, the method includes the step of performing the crosslinking step for the one or monomers, wherein performing the crosslinking step comprises: contacting a metallic gate (e.g., an extended metallic gate) of a field-effect transistor with the one or more monomers [e.g., and one or more salts, electrolytes, and/or mineral acids (e.g., 0.1 M sulfuric acid)]; and applying a potential (e.g., a voltage, e.g., a constant potential, e.g., a time varying potential) or a current (e.g., a constant current, e.g., a time varying current) to the metallic gate of the field-effect transistor to produce the polymer membrane.

In certain embodiments, the method includes the step of performing the crosslinking step for the one or monomers, wherein performing the crosslinking step comprises: contacting the one or more monomers with a photoinitiator (e.g., a UV initiator, e.g., IRGACURE®) [e.g., and a reactive diluent (e.g., hexanediol diacrylate), e.g., and one or more salts, electrolytes, and/or mineral acids] to produce a photo-polymerizable mixture; and optionally, maintaining the portion of the first or second solvent until a portion (e.g., 50% or greater) of the solvent evaporates from the photo-polymerizable mixture; and applying light (e.g., ultraviolet light) to the photo-polymerizable mixture to produce the polymer membrane.

In certain embodiments, the method includes performing the crosslinking step for the one or more monomers, wherein performing the crosslinking step comprises: mixing the one or more monomers with a photoinitiator in a solvent to produce a photo-polymerizable mixture; applying the photo-polymerizable mixture to a surface of a gate of a field-effect transistor; and applying light to the photo-polymerizable mixture to produce the molecularly imprinted polymer membrane.

In one aspect, the present disclosure is directed to a method of manufacturing a molecularly imprinted polymer membrane, the method comprising: contacting a template species with a polymer (e.g., polyvinyl chloride), wherein the polymer is dissolved in a first solvent, to produce a template-containing polymer mixture; applying the template-containing polymer mixture to a surface [e.g., a surface of a metallic gate (e.g., an extended metallic gate) of a field-effect transistor]; allowing the first solvent to evaporate from the applied template-containing polymer mixture; and removing the bound template species from the polymer membrane using a second solvent, wherein the polymer is not substantially soluble (e.g., is not able to be substantially dissolved) in the second solvent, to produce the molecularly imprinted polymer membrane [e.g., wherein the molecularly imprinted polymer membrane comprises a plurality of cavities (e.g., adsorption sites) that are shaped and sized to selectively bind to a molecule of interest (e.g., wherein the molecule of interest is the template species)].

In one aspect, the present disclosure is directed to a biological receptor-functionalized composition, the composition comprising: a biological receptor molecule (e.g., LDL-R or a portion thereof, e.g., HDL-R or a portion thereof) that binds (e.g., is complementary to) to at least a portion of a molecule of interest (e.g., to an apolipoprotein in a lipoprotein); and an immobilization agent [e.g., a polymer matrix, e.g., a carbon chain comprising one or more functional groups for attaching the biological receptor to a surface (e.g., a thiol group, e.g., a carboxy group, e.g., an amine group)] for covalent or non-covalent attachment of the biological receptor molecule to a sensing surface (e.g., a surface of an electrode, e.g., a surface of a gate or extended gate of an FET).

In certain embodiments, the receptor is LDL-R (e.g., or a portion thereof) or HDL-R (e.g., or a portion thereof).

In one aspect, the present disclosure is directed to a biosensor for detecting and/or monitoring a lipoprotein, the biosensor comprising: a surface of a sensor (e.g., a surface of an electrode, e.g., a surface of a gate or extended gate of an FET); a biological receptor molecule (e.g., LDL-R or a portion thereof, e.g., HDL-R or a portion thereof) that binds (e.g., is complementary to) to at least a portion of a molecule of interest (e.g., to an apolipoprotein in a lipoprotein); and an immobilization agent [e.g., a polymer matrix, e.g., a carbon chain comprising one or more functional groups for attaching the biological receptor to a surface (e.g., a thiol group, e.g., a carboxy group, e.g., an amine group)] for covalent or non-covalent attachment of the biological receptor molecule to a sensing surface (e.g., a surface of an electrode, e.g., a surface of a gate or extended gate of an FET).

In certain embodiments, the sensor is an FET. In certain embodiments, the sensor is an electrode, and the biological receptor molecule comprises one or more redox reporters (e.g., methylene blue).

In another aspect, the present disclosure is directed to an apparatus for detecting and/or monitoring one or more molecules of interest in a biofluid. In certain embodiments, the apparatus comprises a field-effect transistor disposed on and/or within a substrate, the field-effect transistor comprising one or more metallic gates; and one or more compositions for selectively sensing at least one of the one or more molecules of interest, wherein: the one or more compositions comprise a molecularly imprinted polymer (MIP) membrane and/or one or more probe materials, and each of the one or more compositions is disposed on at least a portion of a surface of at least one of the one or more gates. In certain embodiments, the molecularly imprinted polymer membrane is manufactured by contacting a template species with one or more monomers; exposing the one or more monomers to a crosslinking agent and/or performing a crosslinking step for the one or more monomers to produce a polymer membrane, said polymer membrane comprising bound template species; and removing at least a portion of the bound template species from the polymer membrane to produce the molecularly imprinted polymer membrane.

In certain embodiments, the one or more monomers comprises a functional group selected from the group consisting of an amine group, a thiol group and a carboxy group. In certain embodiments, the one or more monomers comprises ethylene and/or propylene. In certain embodiments, the template species comprise one or more molecules of interest.

In certain embodiments, the one or more monomers comprise one or more members selected from the group consisting of: an electrochemically polymerizable monomer, a photocurable monomer, and a chemically polymerizable monomer.

In certain embodiments, the one or more monomers comprises a member selected from the group consisting of aminophenyl boronic acid, phenyl boronic acid, acrylamide, aniline, and pyrrole.

In certain embodiments, the one or more monomers comprises a member selected from the group consisting of styrene and oligomeric acrylate.

In certain embodiments, the one or more monomers comprises a member selected from the group consisting of 3-aminophenyl boronic acid, N-methacryloyl-(L)-tyrosine methyl ester, and methacrylic acid.

BRIEF DESCRIPTION OF THE DRAWINGS

The foregoing and other objects, aspects, features, and advantages of the present disclosure will become more apparent and better understood by referring to the following description taken in conjunction with the accompanying drawings, in which.

Figure 1:
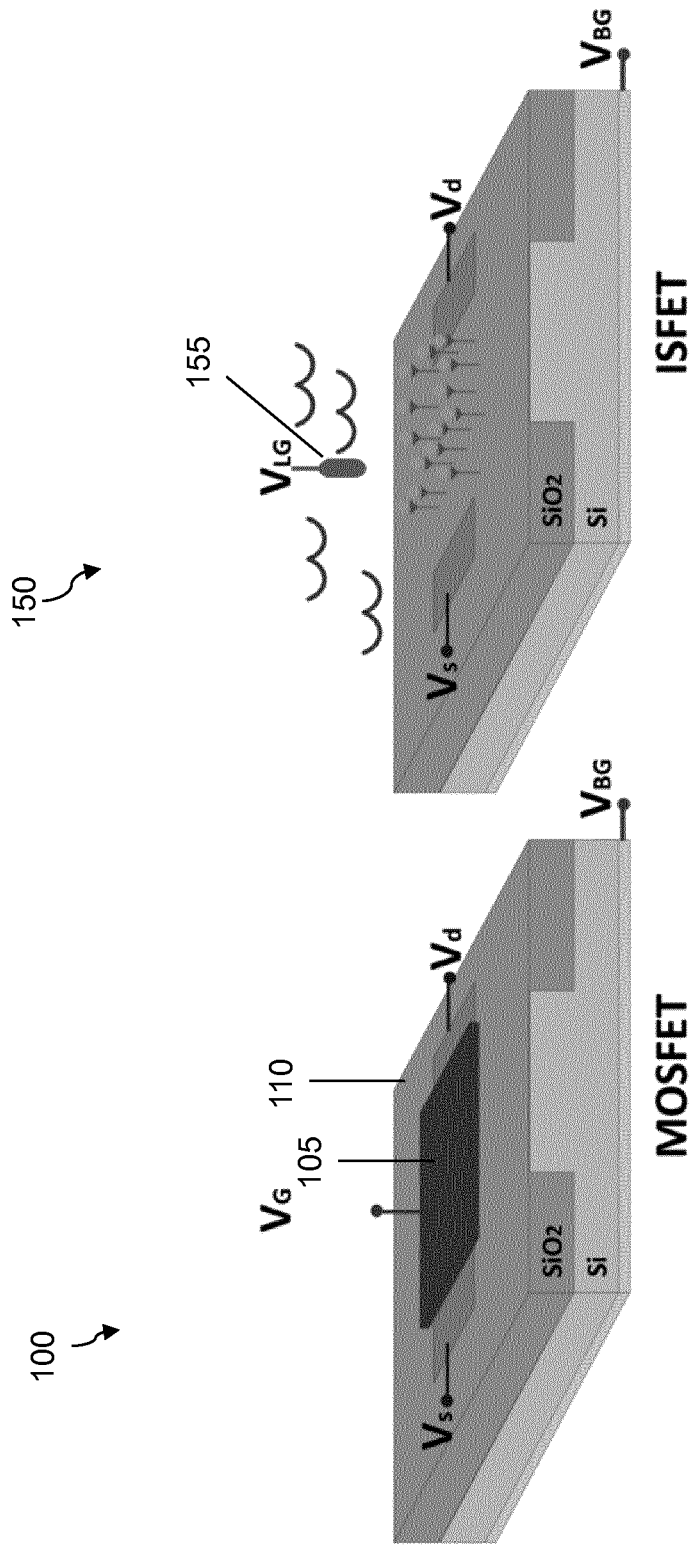
FIG. 1 is a depiction of illustrative examples of a MOSFET and an ISFET.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

Elements of embodiments described with respect to a given aspect of the invention may be used in various embodiments of another aspect of the invention. For example, it is contemplated that features of dependent claims depending from one independent claim can be used in apparatus, articles, systems, and/or methods of any of the other independent claims.

Headers are provided for the convenience of the reader—the presence and/or placement of a header is not intended to limit the scope of the subject matter described herein.

As used herein, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) where ranges are provided, endpoints are included.

As used herein, the terms "about" or "approximately", when used herein in reference to a value, refers to a value that is similar, in context to a referenced value. In general, those skilled in the art, familiar with the context, will appreciate the relevant degree of variance encompassed by "about" or "approximately" in that context. For example, in some embodiments, the terms "about" or "approximately" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

As used herein, the term "continuous," as in a continuous biomarker measurement, refers to performing a series of measurements (e.g., of the presence and/or quantity of a biomarker) without a substantial time interval between each measurement. For example, continuous measurements may be performed at a rate of one measurement every ten minutes, one measurement every five minutes, one measurement per minute, one measurement every 30 seconds, one measurement every 5 seconds, or faster rates.

In certain embodiments, a continuous measurement can occur in substantially "real-time" such that the concentration value of an analyte measured by the device is the concentration present in sweat without a substantial delay or latency on the timescale of physiological processes (e.g., on a scale of five minute or greater). For example, the device may display a "snapshot" of the concentration of an analyte in the biofluid (e.g., every 5 minutes, 1 minute, 30 seconds or less). In certain embodiments, the continuous measurements are performed at a higher frequency (e.g., every second or every several milliseconds) providing a continuous analyte data stream faster than the physiological timescale.

As used herein, the term "substantially" refers to the qualitative condition of exhibiting total or near-total extent or degree of a characteristic or property. For example, a substantially constant value may vary in time by 20%, 15%, 10%, 9%, 8%, 7%, 6%, 5%, 4%, 3%, 2%, 1%, or less of the constant value.

Details regarding various embodiments of an apparatus for detecting and/or monitoring one or more molecules of interest (e.g., cytokines, e.g., cholesterol) are presented herein. In certain embodiments, an apparatus for detecting and/or monitoring one or more molecules of interest comprises one or more metallic gates (e.g., an extended metallic gate) of a field-effect transistor and one or more compositions comprising a molecularly imprinted polymer (MIP) membrane. For each of the one or more metallic gates, one or more of the compositions is disposed on (e.g., fully or partially covers) a surface of the metallic gate. The molecularly imprinted polymer of the composition enables the detection of a specific target analyte (e.g., an analyte of interest in a liquid sample that comes into contact with the molecularly imprinted polymer. In certain embodiments, the target analyte is a cytokine.

In certain embodiments, the apparatus described herein further include an interface and/or interface surface comprising at least one biocompatible material for contacting a body part, at least one inlet for receiving a biofluid; at least one outlet for evacuating the biofluid; and at least one microfluidic and/or nanofluidic channel in fluid communication with the at least one inlet, at least a portion of the one or more compositions (e.g., the molecularly imprinted polymer) and/or the aptamers disposed on the one or more metallic gates of the field-effect transistor, and the at least one outlet. For example, the apparatus may include the systems, methods, devices, apparatus, and architectures presented herein are described in European Patent Application No. 16188227.9 filed Sep. 10, 2016, U.S. patent application Ser. No. 15/453,920 filed Mar. 9, 2017, International Patent Application No. PCT/182017/055456, filed Sep. 11, 2017, U.S. patent application Ser. No. 15/913,714 filed Mar. 6, 2018, and International Patent Application No. PCT/EP2018/077793, filed Oct. 11, 2018, the contents of which are incorporated herein in their entirety.

The apparatus described herein for detecting and/or monitoring one or more molecules of interest can be used by contacting a solution (e.g., a biofluid such as sweat or blood) with one or more of the compositions described herein. The compositions can include a molecularly imprinted polymer and/or probe materials (e.g., receptors and/or aptamers), which are disposed on a surface of the metallic gate of a field-effect transistor. An electrical signal from the apparatus (e.g., a current or voltage measured at the field-effect transistor, e.g., a drain voltage, e.g., a drain current) is detected and/or monitored (e.g., continuously, e.g., in real time) using an electronic circuit of the apparatus. The detected and/or monitored electrical signal is indicative of the presence of and/or a concentration (e.g., an amount) of the target analyte in the solution.

The apparatus described herein include one or more field-effect transistors (FETs) (e.g., or one or more arrays of FETs). An example of an FET is an ion-sensitive field-effect transistor (ISFET), which can be used for pH and ion measurements. An ISFET is analogous to a planar metal oxide semiconductor field-effect transistor (MOSFET) in which the gate dielectric is exposed to a solution.

FIG. 1 shows illustrative examples of a MOSFET 100 and an ISFET 150. A gate electrode 150 of MOSFET 100 is in contact with the gate dielectric 110. In ISFET 150, a local-gate ($L_G$) electrode 155 (e.g., a reference electrode) is inserted into the liquid that is in contact with the gate and used a reference to measure or apply a local-gate voltage ($V_{LG}$). Ions in solution or charged molecules can influence the gate voltage and alter the source to drain current ($I_d$). The presence and/or quantify of the ions can be sensed through the change in gate voltage and/or source-to-drain current.

For example, when molecules are adsorbed on the surface of an ISFET, a surface potential ($\varphi_0$) is generated on the gate material (e.g., the gate oxide) resulting in a threshold voltage ($V_{th}$) change of the ISFET according to:

$$V_{th} = V_{Ref} - \varphi_0 + X^{sol} - \frac{\phi_{Si}}{q} - \frac{Q_{ox} + Q_{ss} + Q_s}{C_{ox}} + 2\phi_f$$

where $V_{Ref}$ is the potential of the a local-gate ($L_G$) electrode (e.g., a reference electrode), $\chi_{sol}$ is the dipole moment of the liquid in contact with the gate, $\phi_0$ is the surface potential generated on the gate material by adsorbed analytes, $\phi_{Si}$ is the silicon work function, q is the elementary charge, $Q_{ox}$ is the gate oxide charge, $Q_{SS}$ is the interface charge, $Q_B$ is the depletion layer charge, $C_{ox}$ is the gate oxide capacitance per unit area, and $\phi_f$ is the Fermi potential. For a fixed $V_{Ref}$, only the surface potential $\varphi_0$ changes as a function of the concentration of charged molecules. $V_{Ref}$ can be set to a fixed value to operate an FET in a so-called subthreshold slope regime to provide improved sensitivity.

The present disclosure relates, in certain embodiments, to modifying the surface of the gate (e.g., a metallic gate, an extended metallic gate, or a gate dielectric) of an FET (e.g., the sensing surface of an ISFET) using specifically designed compositions that cover a portion (up to all) of the gate. Molecules (e.g., cytokines, e.g., cholesterol, e.g., lipoprotein) in a liquid with which the functionalized surface is in contact can be sensed (e.g., the presence and/or quantity of the molecule(s) can be determined) from measurements of an electrical signal received from the FET. For example, the drain voltage and/or the drain current of the FET can be measured to sense molecules (e.g., cytokines, e.g., cholesterol, e.g., lipoprotein) in the liquid that have interacted with (e.g., adsorbed to, e.g. bound to) the gate. For example, an impedance of the FET can be measured (e.g., at one or more frequencies) to sense molecules (e.g., cytokines, e.g., cholesterol, e.g., lipoprotein) in the liquid that have interacted with (e.g., adsorbed to, e.g. bound to) the gate.

Examples of FET sensors which may be used in the systems, methods, devices, apparatus, and architectures presented herein are described in European Patent Application No. 16188227.9 filed Sep. 10, 2016, U.S. patent application Ser. No. 15/453,920 filed Mar. 9, 2017, and U.S. patent application Ser. No. 15/913,714 filed Mar. 6, 2018, the contents of which are incorporated herein in their entirety.

Figure 2:
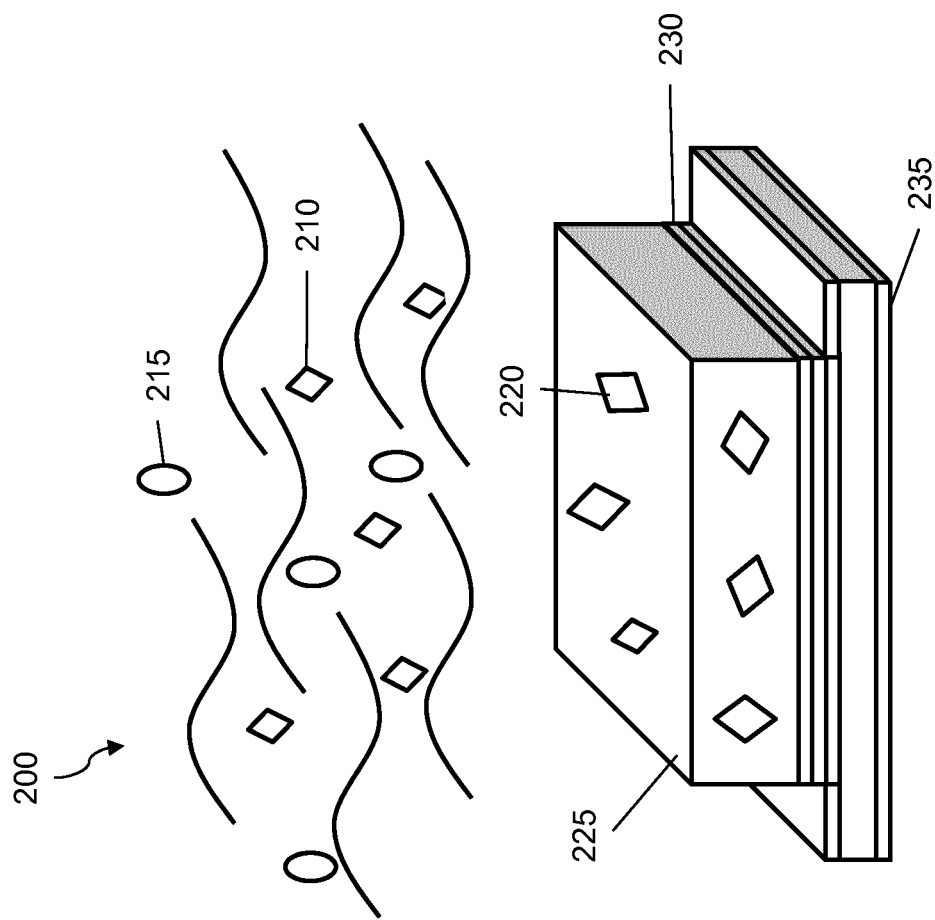
FIG. 2 is a diagram depicting a molecularly imprinted polymer disposed on the metallic gate of an FET, according to an illustrative embodiment.

In certain embodiments, the surface of an FET gate or extended gate are functionalized with a molecularly imprinted polymer (MIP) that covers a portion (up to all) of the surface of the dielectric or metallic gate (e.g., or extended gate) of an FET sensor. FIG. 2 shows an illustrative example 200 of an MIP 225 disposed on a direct metallic gate 230 of an FET 235. MIP 225 includes a plurality of adsorption sites 220 (e.g., cavities) that are designed (e.g., shaped and sized) to have an affinity for one or more particular molecules of interest 210 (e.g., target analyte(s)). MIP 225 does not have an affinity for other molecules 215 in the fluid. A direct gate MIP-based field-effect transistor 235 (MIP-gate FET) can thus be used to selectively detect a molecule of interest 210 (e.g., a cytokine) in a liquid (e.g., in an aqueous sample, e.g., a biofluid such as sweat).

Figure 3:
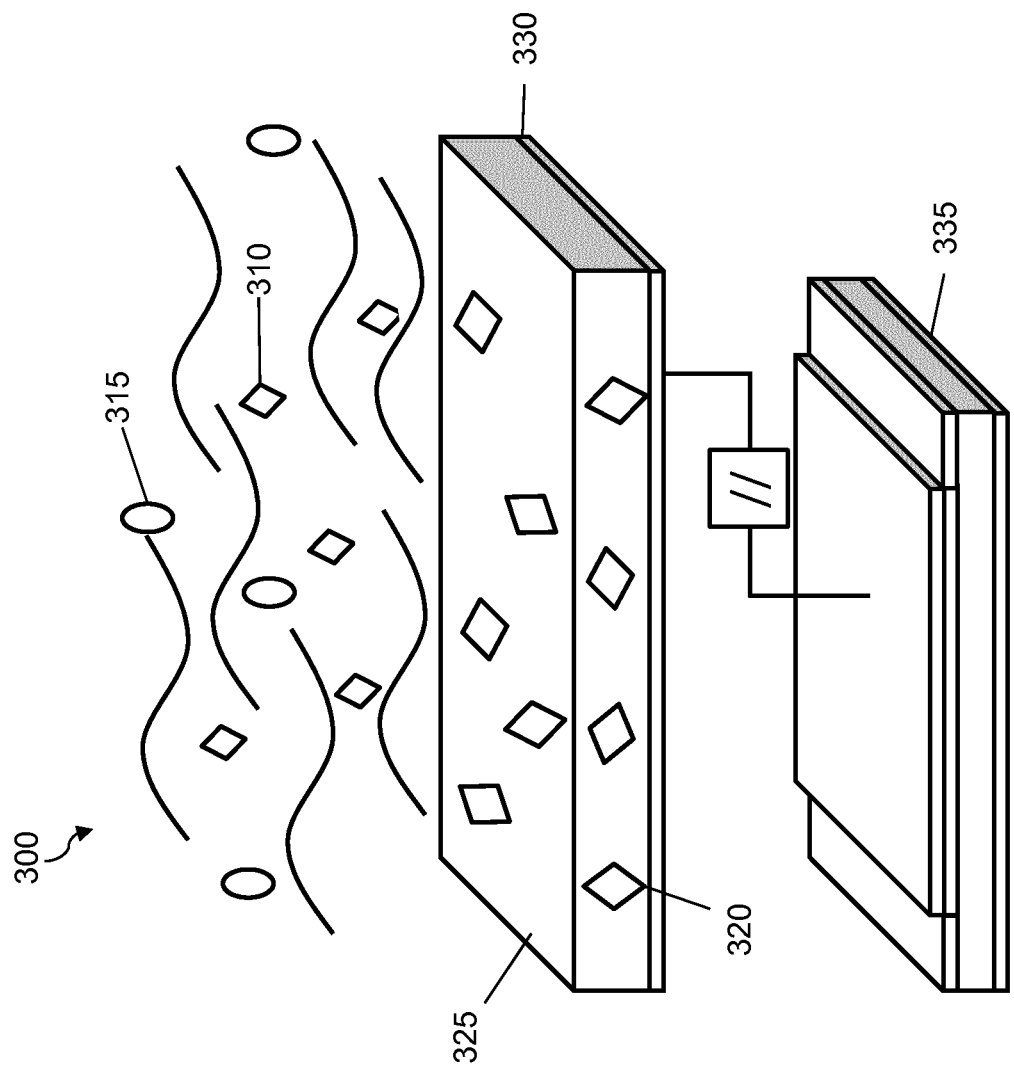
FIG. 3 is a diagram depicting a molecularly imprinted polymer disposed on the extended metallic gate of an FET, according to an illustrative embodiment.

FIG. 3 shows an illustrative example 300 of an MIP 325 disposed on an extended metallic gate 330 of an FET 335. MIP 325 includes a plurality of adsorption sites 320 (e.g., cavities) that are designed (e.g., shaped and sized) to have an affinity for one or more particular molecules of interest 310 (e.g., target analyte(s)). MIP 325 does not have an affinity for other molecules 315 in the fluid. An extended gate MIP-based field-effect transistor 335 (MIP-gate FET) can thus be used to selectively detect a molecule of interest 310 (e.g., a cytokine) in a liquid (e.g., in an aqueous sample, e.g., a biofluid such as sweat).

In certain embodiments, the MIP is disposed on a metallic gate or a gate dielectric of an FET. For example, as shown in the illustrative example of FIG. 2, the FET sensor transduction surface (e.g., the MIP-functionalized metallic gate) can be a metallic layer disposed directly on top of the gate dielectric of an FET. In other embodiments, the MIP membrane is disposed on the gate dielectric (e.g., the FET does not include a metallic gate). The metallic gate (e.g., the direct or extended metallic gate) of an FET can be covered or partially covered by an MIP. For example, the MIP can cover a surface area of a metallic FET gate in range from about 10% to about 100% of the total surface area of the metallic gate. For example, the MIP may cover 10%, 20%, 30%, 40%, 50%, 60%, 70%, 80%, 90%, or 100% of the surface area of the metallic gate of the FET.

In other embodiments, an MIP covers or partially covers an extended metallic gate of an FET. For example, as shown in the illustrative example of FIG. 3, the metallic gate can be spatially separated from (but operatively connected to) the gate dielectric of an FET. The use of an extended gate can decrease manufacturing complexity (e.g., and costs), can streamline manufacturing, and can facilitate improved sensing (e.g., detection and/or quantification) of analytes. For example, the field-effect transistor can be manufactured in a front-end process. The front-end process might be performed in bulk (e.g., and using established processes) to reduce costs. One or more transduction surfaces (e.g., extended metallic gates covered or partially covered with an MIP) can be disposed on the devices in a back-end process. For example, transduction surfaces can include a metallic grid covered or partially covered with an MIP. In certain embodiments, an extended metallic gate has a larger sensing surface area (e.g., for improved sensing of target analytes) than that of a direct metallic gate.

As with the direct metallic gate, the extended metallic gate of an FET can be covered or partially covered by an MIP. For example, the MIP can cover a surface area of an extended metallic FET gate in range from about 10% to about 100% of the total surface area of the metallic gate. For example, an MIP may cover 10%, 20%, 30%, 40%, 50%, 60%, 70%, 80%, 90%, or 100% of the surface area of the metallic gate of the FET.

In certain embodiments, the MIP membrane-based sensors described herein may undergo less degradation, be more stable (e.g., during use over time), be capable of operating under a broad range of conditions (e.g., in liquids with a broad range of pH values, temperatures, ionic strengths, and the like) than previous sensors based on, for example, biological compounds such as antibodies and aptamers.

In certain embodiments, the MIP-gate FET sensors described herein provide for more selective and higher sensitivity sensing (e.g., detection and/or quantification) of cytokines in a biofluid (e.g., human sweat) than is possible using previous technologies.

Preparation of MIP Membranes

Described herein are various methods for preparing an MIP membrane (e.g., an MIP membrane disposed on the gate of an FET or an MIP-gate FET) for sensing molecules (e.g., cytokines) in a biofluid (e.g., sweat).

MIP membranes are, in certain embodiments, directly synthesized on a portion (up to all) of the surface of a gate or an extended gate of an FET device. For example, a mixture comprising one or more monomers (e.g., one or more functional monomers and/or one or more structural monomers) and template species can be contacted with a portion (up to all) of the gate (e.g., or extended gate) of the FET. The template species can include one or more of the molecules of interest (e.g., molecules that are the same as or share properties (e.g., of shape, size, chemical functionality) with the target analyte). Each functional monomer includes a functional group [e.g., a chemical or biochemical functional group (e.g., an amine group, e.g., a thiol group, e.g., a carboxy group, e.g., a 3D structure) that binds or coordinates to a defined (e.g., adsorption) site of the template species]. Examples of structural monomers include ethylene, propylene, and other monomers of commonly used polymers. In certain embodiments, at least one of the functional monomers is selected to bind with an adsorption site of the template species. When the one or more monomers include at least one functional monomer, the one or more monomers are contacted together with (e.g., mixed with) the template species to form a monomer-template complex. The monomer-template complex includes a template species with one or more functional monomers bound to or complementing a defined (e.g., adsorption) site(s) thereon. When the one or more monomers do not include a functional monomer (e.g., when the one or more monomers include one or more structural monomers), the monomers are contacted together with the template species. The one or more monomers are then polymerized to form a polymer membrane that includes bound (e.g., chemically and/or physically bound) or embedded template species. For example, functional monomers may both chemically and physically bind the template species to the polymer. For example, structural polymers may physically bind or embed the template species to the polymer. The template species are then removed from the polymer membrane (e.g., through physical and/or chemical means).

Figure 4:
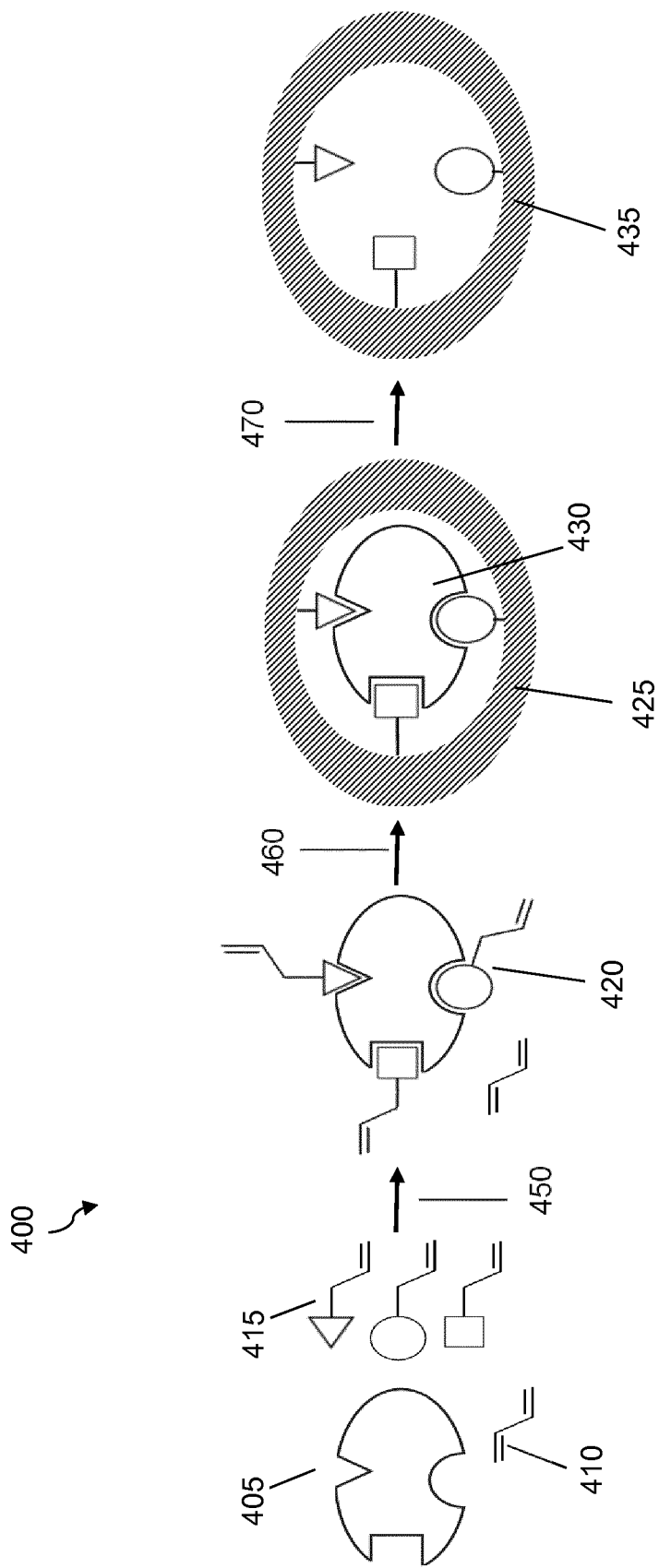
FIG. 4 is a reaction diagram depicting a method for preparing a molecularly imprinted polymer, according to an illustrative embodiment.

An illustrative example of a method 400 for preparing an MIP is shown in FIG. 4. In this example, a template species 405 (e.g., a target molecule, e.g., a molecule of interest, e.g., a molecule that includes functional groups or other molecular sites of interest) is complexed with a plurality of monomers, which may include one or more functional monomers 415 and/or one or more structural monomers 410 to produce a monomer-template complex 420 (Step 450). The monomers (410 and 415) in monomer-template complex 420 and the structural polymers are then crosslinked (Step 460). After crosslinking, a resulting polymer membrane 425 includes a bound template species 430. Bound template species 430 is removed (Step 470) via washing (e.g., to remove the physically trapped template species), through a proteinase digestion (e.g., to break chemical bonds between the functional monomers and the template species), and/or through an oxidation of polymer membrane 425. After the template species is removed, the resulting material is a molecularly imprinted polymer (MIP) membrane 435.

The MIP membrane includes cavities (e.g., adsorption sites) that are sized and shaped similarly to the template species. These cavities (e.g., adsorption sites) are complementary (e.g., in size and shape) to one or more molecules of interest (e.g., target analyte(s)). Such an MIP membrane, when disposed, for example, on the metallic gate, extended metallic gate, or gate dielectric of an FET, can be used to selectively sense the concentration and/or rate of adsorption of target analytes (e.g., molecules of interest) to these cavities (e.g., adsorption sites).

In various embodiments, as described in the illustrative examples below, an MIP is prepared [e.g., on a portion (up to all) of a gate or an extended gate of an FET] using electropolymerization, photo-polymerization, deposition, and/or polymerization (e.g., addition polymerization, e.g., condensation polymerization).

Example Method 1: Molecularly Imprinted Polymer Membranes Via Electro-Polymerization Electrochemical polymerization (or electropolymerization) allows MIP membranes to be prepared on sensor surfaces with a high level of spatial control. Thus, electropolymerization allows each sensor of an array of closely spaced miniaturized sensors to include an MIP that is used for sensing a different molecule of interest. An electrochemically polymerized MIP membrane can be directly grown on the metallic gate of an FET by using the metallic as an electrode. Monomer(s) (e.g., one or more of aminophenyl boronic acid, phenyl boronic acid, acrylamide, aniline, and pyrrole) can be used to prepare an MIP membrane via electrochemical polymerization (e.g., electro-polymerization). A cytokine-sensitive MIP can be prepared using the following approach.

A three-compartment electrochemical cell is used that includes an auxiliary electrode [e.g., a counter electrode, a reference electrode (e.g., an Ag/AgCl reference electrode)], and an FET gate (e.g., a metallic FET gate) operated as a working electrode. A solution of 0.1 M to 0.15 M 3-aminophenyl boronic acid (APBA) and 0.1 M to 0.75 M of interleukin IL-6 in 0.1 M sulfuric acid is used to synthesize, via electro-polymerization, a boronate-functionalized polyaniline membrane that includes a plurality of interleukin IL-6 molecules.

Electro-polymerization is performed by cycling (e.g., increasing and decreasing) the potential applied to the working electrode at a rate (e.g., a sweep rate) of 40 mV/s. The potential may be swept, for example, between −5 to +5 V vs Ag/AgCl (saturated). For example, the potential of the working electrode (the gate of the FET) can be cycled for between 1 and 1000 cycles to perform electropolymerization. In certain embodiments, the potential of the working electrode (the gate of the FET) is cycled for about 5 or less, about 10 or less, or about 20 or fewer times to perform electropolymerization (e.g., to obtain an electropolymerized membrane with an appropriate thickness for sensing molecules of interest). Following the electro-polymerization reaction, the resulting membrane is washed (e.g., using DI water, a solution comprising water, or another solvent) to remove the interleukin IL-6 molecules, resulting in an MIP membrane with a plurality of cavities, each shaped substantially like an interleukin IL-6 molecule.

Example Method 2: Molecularly Imprinted Polymer Membranes Via Photopolymerization Photopolymerization allows MIP membranes to be prepared on sensor surfaces with a high level of spatial control. Thus, photopolymerization allows each sensor of an array of closely spaced miniaturized sensors to include an MIP that is used for sensing a different molecule of interest. Light-sensitive monomers can be polymerized on the surface of a gate (e.g., a semiconductor or metallic gate, or extended gate) of an FET. For example, light-sensitive monomers can be photopolymerized using a specific wave-length (e.g., and power) of light to initiate the formation of a polymer membrane. Examples of light-sensitive (e.g., photo-sensitive) monomers that can be used to prepare the MIP membranes described herein include styrene and oligomeric acrylate. An example of a method for preparing a photocurable, cytokine-sensitive MIP membrane is provided in the following:

A first solution comprising diacrylate oligomer and a UV initiator (e.g., IRGACURE®) is homogenized in hexanediol diacrylate. An amount (e.g., 0.3 g) of this mixture is then solubilized in a volume (e.g., 2 mL) of a solvent (e.g., tetrahydrofurane). Template species (e.g., molecules of interest, e.g., target analyte molecules, e.g., molecules with a similar shape, size, and/or molecular structure to a target analyte) are added to the mixture. A drop of this mixture is applied (e.g., drop-casted) on the surface FET gate (e.g., at least a portion of the surface). The drop is maintained until the solvents evaporate, and the resulting film is exposed to ultraviolet (UV) light to crosslink the material and form the membrane (e.g., to form a cross-linked matrix). The template species (e.g., interleukin IL-6 molecules) are subsequently removed from the polymer matrix, for example, by digestion using a proteinase to form an MIP membrane with a plurality of active sites (e.g., cavities shaped and sized like the template species).

Example Method 3: Molecularly Imprinted Polymer Membrane(s) Via Deposition (e.g., Drop Casting)

An MIP can be prepared via the deposition (e.g., drop-casting) of a dissolved polymer (e.g., without requiring a polymerization reaction). A mixture of polymers that are not substantially water soluble (e.g., polyvinyl chloride) can be mixed with template species in an appropriate organic solvent and deposited (e.g., via drop-casting) on the gate of an FET. The solvent is then allowed to evaporate to form a polymer membrane (e.g., a membrane of polyvinyl chloride). The template species are then removed, for example, by washing the membrane with a co-solvent to prepare the MIP membrane. The co-solvent is selected in which the template species are soluble but the polymer is insoluble in order to prevent the membrane dissolution leading to its loss of selectivity.

Example Method 4: Molecularly Imprinted Polymer Membrane(s) Via Polymerization

An MIP can be prepared via the polymerization of functional monomers (e.g., 3-aminophenyl boronic acid, N-methacryloyl-(L)-tyrosine methyl ester, and/or methacrylic acid) in the presence of template species and a chemical initiator. A method for the preparation of an MIP for sensing a cytokine such as interleukin IL-6 or IL-10 is presented below.

A precursor solution that includes template species (e.g., IL-6 or IL-10 molecules) and functional monomers [e.g., 3-aminophenyl boronic acid (APBA)] is prepared at a 1:1 mol ratio in phosphate buffer (pH 7.2). The precursor solution is contacted together (e.g., mixed) with the cross-linker methylene bisacrylamide (MBA) and 1 mg/mL ammonium persulfate. The chemical initiator N,N,N',N" tetramethylenebisacrylamide (TEMED) is then added to the mixture. A drop of this mixture is deposited on the gate of the FET, and polymerization is performed at 37° C. for 90 min. The template species (e.g., IL-6 or IL-10 molecules) are subsequently removed from the polymer matrix via a proteinase digestion to form an MIP.

Use of an MIP for Molecular Sensing

Physicochemical properties of an MIP change as a function of the amount of target molecules adsorbed on an MIP and/or on the rate at which the molecules of interest adsorb on the MIP. An MIP can thus be used to monitor the amount and/or adsorption rate of molecules interest by measuring changes in physicochemical properties of the MIP. Changes in physicochemical properties of the MIP are measured via corresponding changes in an electrical signal from the FET. For example, the electrical potential of an MIP, in certain embodiments, changes as a function of the concentration of a target molecule in a liquid medium in contact with the MIP, and the electrical potential of the FET is thus measured to sense the target molecule. In certain embodiments, an electrical impedance of the MIP changes as a function of the concentration of a target molecule in a liquid medium in contact with the MIP, and the electrical impedance of the FET is thus measured to sense the target molecule. When an MIP is disposed on a portion (up to all) of a gate (e.g., or an extended gate) of an FET, as in the systems and methods described herein, changes in the electrical potential and/or electrical impedance of the MIP disposed on the gate of the FET can be monitored (e.g., sensed, e.g., continuously sensed) by measuring changes in the FET gate potential and/or impedance. For example, changes in the FET gate potential can be measured by monitoring changes in the electrical conductivity of the FET via a readout of drain current or drain voltage as a function of time. The characteristics of the drain current or drain voltage can be correlated to the concentration of a target molecule in the liquid medium (e.g., by performing a series of calibration measurements). Thus the MIP-gate FET may be used as a biochemical sensor.

Figure 5:
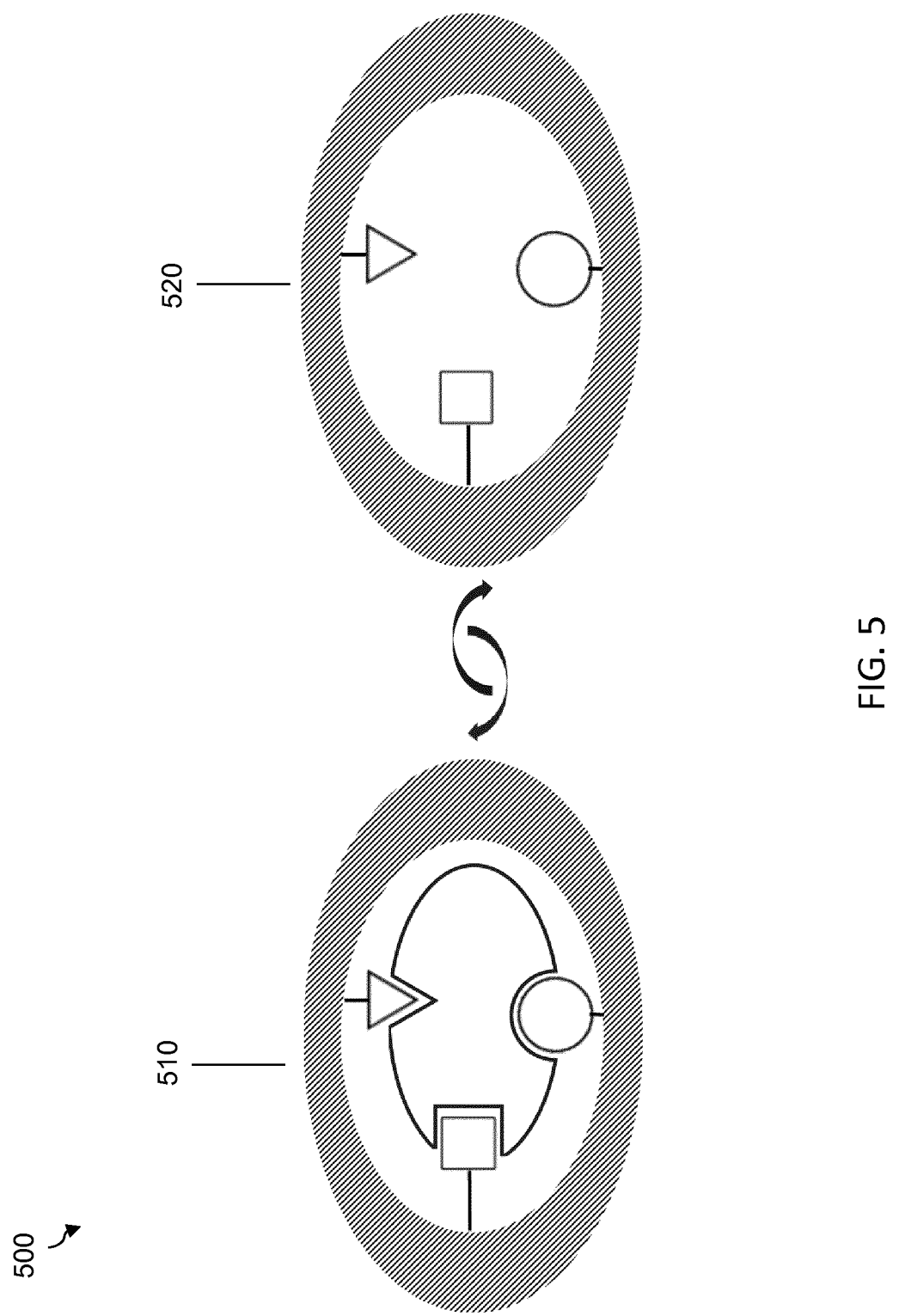
FIG. 5 is a diagram depicting the adsorption and removal of a target analyte from an adsorption site of a molecularly imprinted polymer, according to an illustrative embodiment.

In certain embodiments, an MIP may be reused over time to repeatedly monitor the concentration of a target analyte (e.g., a molecule of interest). For example, various resetting processes can be used to remove an adsorbed target analyte, facilitating the repeated use of the MIP for sensing applications. For example, molecule-solvent affinity cleaning can be used to remove target analytes from the MIP. For example, target analytes can, in certain embodiments, be removed from the MIP using electrochemical approaches such as oxidation (e.g., over-oxidation) of the MIP by passing a current through the metallic gate of the FET. FIG. 5 is an illustrative diagram showing a process 500 of the binding and unbinding of a target analyte to an adsorption site of an MIP. For example, MIP 510 with a bound molecule of interest can be overoxidized to remove the bound or adsorbed molecule of interest in order to obtain the MIP 520 without a bound molecule of interest. MIP 520 can thus be used for subsequent measurement.

Probe-Functionalized Compositions Useful for Lipoprotein Sensing

Figure 6:
FIG. 6 is an illustration depicting a model of apolipoprotein B100.

LDL-Cholesterol (LDL-Ch), is popularly known as "bad cholesterol". Apolipoprotein B, which is encoded by the APOB gene located on the 2nd chromosome, is the main apolipoprotein of LDL particles. FIG. 6 (adapted from Jere P. Segrest et al., *Journal of Lipid Research*, 2001; 42:1346-1367) shows an illustration of an X-ray crystal structure 600 of a lipid-protein complex that is similar to apolipoprotein B. LDL-Ch delivers fat molecules to cells, and high LDL-Cholesterol concentrations in the blood are associated with the progression atherosclerosis and the buildup of fatty plaque in arteries. This buildup narrows arteries and increases an individual's risk of cardiovascular disease, heart attack, and stroke.

Figure 7:
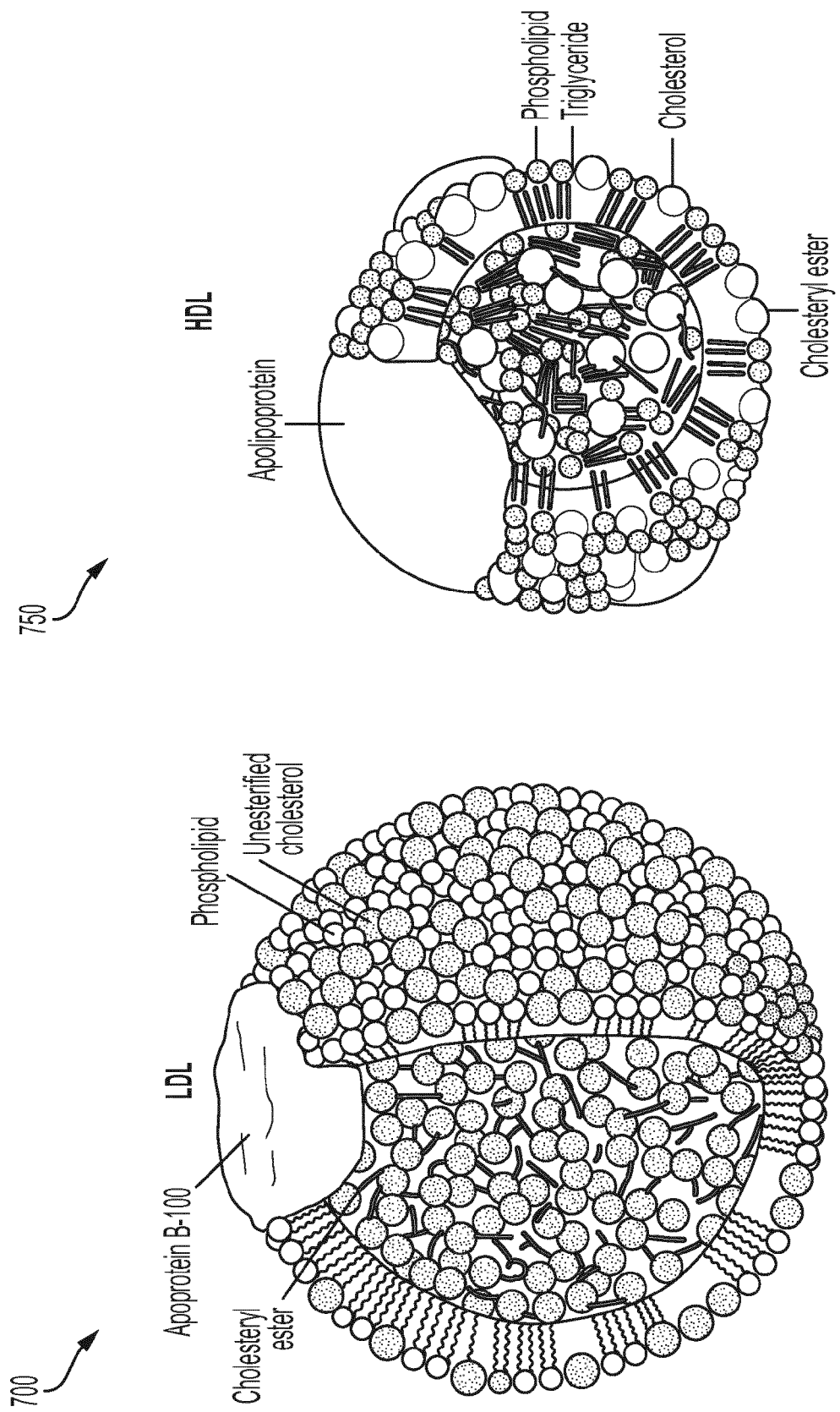
FIG. 7 is an illustration depicting low density lipoprotein (LDL) and high density lipoprotein (HDL)

FIG. 7 shows an illustration of low-density lipoprotein (LDL) 700 (adapted from Ilene Sutter, "The what-what on LDL/HDL (that's your blood lipids)", https://foodspace.wordpress.com/2008/05/27/the-what-what-on-ldlhdl-thats-your-blood-lipids/). LDL is one of the five majors groups of lipoproteins which transport fat molecules in the extracellular fluid of the body. Lipoproteins are complex proteins composed of multiple proteins. LDL particles are composed of a single apolipoprotein B-100 molecule comprising phospholipids, triglycerides, and cholesterol.

HDL-Cholesterol (HDL-Ch) is popularly known as "good cholesterol". Apolipoprotein A1, which is encoded by the APOA1 gene located on the $11^{th}$ chromosome, is the major protein component of HDL particles. HDL-Cholesterol acts as a scavenger. HDL-Ch removes fat and lipid molecules including cholesterol by transporting them away from cells to the liver. HDL-Cholesterol is associated with a decrease in atherosclerosis build-up in the endothelium and inner walls of arteries.

FIG. 7 shows an illustration of high-density lipoprotein (HDL) 750 (adapted from https://www.mybiosource.com/assay-kits/hdl-cholesterol/168359#QLAPP_MBS168359_TD). HDL is one of the five major groups of lipoproteins. HDL typically comprises 80 to 100 proteins organized by one, two or three ApoA, depending on their size. Each LDL particle transports up to hundreds of lipid molecules. The lipids carried include cholesterol, phospholipids, and triglycerides, in a variable ratio. HDL is the smallest of the lipoprotein particles. HDL is the densest because it contains the highest proportion of proteins to lipids. The most abundant apolipoproteins of HDL are apolipoprotein A-I and apolipoprotein A-II.

Currently, the determination of LDL concentration is usually obtained via an indirect measurement in which the amount of cholesterol bound to LDL particles (LDL-Ch) is estimated using the Friedewald calculation. Using the Friedewald calculation, the LDL-Ch concentration is estimated by subtracting the cholesterol linked to other lipoproteins from the total cholesterol. The Friedewald calculation requires three independent lipid analyses. The amount of cholesterol in samples is determined enzymatically (e.g., cholesterol esterase and cholesterol oxidase), and the various class of lipoproteins are separated physically using surfactants and/or centrifugation processes.

Figure 8:
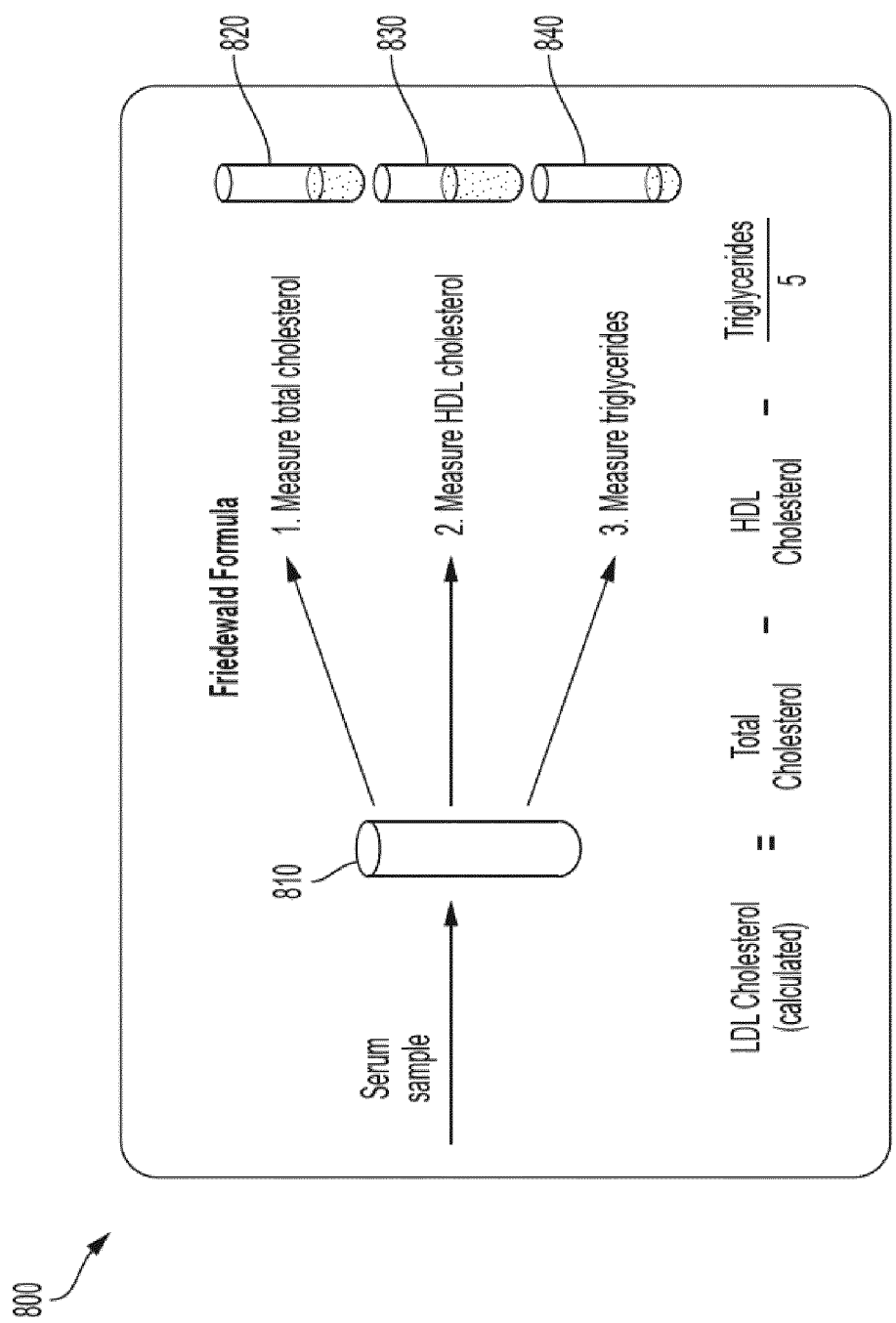
FIG. 8 is a diagram depicting the Friedewald calculation for estimating LDL-cholesterol (LDL-Ch) levels using existing techniques.

FIG. 8 shows an illustrative example of a method 800 of performing the Friedewald calculation using a serum sample 810, which is divided into at least three separate samples, which include a sample 820 for measuring total cholesterol, a sample 830 for measuring HDL-Cholesterol, and a sample 840 for measuring triglycerides.

The Friedewald calculation for estimating LDL-Ch is:

VLDL-Ch=Triglycerides/5

LDL-Ch=total cholesterol−(HDL-Ch+VLDL-Ch)

Using the Friedewald calculation for determining levels of LDL cholesterol has several limitations or drawbacks, which include: i) the amount of LDL is estimated by calculation; ii) multiple assays and multiple steps are required, each adding a potential source of error; iii) since no direct very low density lipoprotein-cholesterol (VLDL-Ch) assay is available, the concentration of VLDL is estimated by dividing the triglyceride value by a factor of 5 (as shown in the equation above); iv) measurements of LDL-Ch via the Friedewald calculation require that patients fast for 12 to 14 hours prior to specimen collection to avoid a triglyceride bias; v) LDL measurements performed using the Friedewald calculation are not standardized; and vi) the Friedewald calculation becomes increasingly inaccurate at borderline triglyceride levels (200-400 mg/dL or 2.3-4.5 mmol/L).

Nuclear magnetic resonance (NMR) spectroscopy can be used to measure LDL levels. However, NMR tests require the use of expensive, complex tools and resources that are not commonly accessible. These NMR tools and resources are often only available in a few laboratories. NMR tests are thus not accessible to most users and cannot be used for real-time, long-term, or low-cost monitoring of lipoprotein levels.

Indirect and direct measurements of LDL are not always correlated in the same and can be discordant (e.g., indirect measurements of LDL via the concentration of LDL-Ch do not always accurately reflect the concentration of LDL). Although it would be beneficial to directly measure LDL, current technology for directly measuring LDL concentration (e.g., NMR spectroscopy) LDL has a high cost and a low availability. The importance of measuring LDL directly is increased under several conditions that are important for improving human health. For example, the Friedewald calculation becomes irrelevant in non-common pathologies or in out of scale values.

The probe-functionalized compositions described herein for sensing lipoproteins allow for new, fast, accurate and reversible biosensors for the direct and continuous measurement of LDL in biofluids. In certain embodiments of the compositions and biosensors described herein, cholesterol amount can be determined by using a probe that targets the apolipoprotein B100. This apolipoprotein is especially useful for measuring lipoproteins in people who have elevated Triglyceride levels, which otherwise make it difficult to accurately measure their LDL levels. It should be appreciated by a one of ordinary skill in the art, that the compositions, biosensors, apparatus, and methods described herein can be used with minor modifications for the direct measurement of high-density lipoprotein (HDL) or HDL-Ch by using an appropriate probe molecule (e.g., a specific aptamer or a specific protein receptor compatible with apolipoprotein A).

The probe-functionalized compositions described herein (e.g., which comprise aptamers or specific protein receptors for the detection of a lipoprotein of interest) can be used to directly sense (e.g., detect and/or quantify) LDL-Ch or LDL by disposing the composition on a sensing surface such as the surface (e.g., the gate dielectric, e.g., a metallic gate or an extended metallic gate) of an FET or the surface of an electrode. This approach permits the miniaturization of the biosensor devices and apparatus such that they can be easily transported, manufactured at a low cost, and used in a conveniently wearable manner.

Additionally, the probe-functionalized compositions can be used in miniaturized (e.g., and reversible) biosensors for the analysis of biofluids in a user-friendly fashion. For example, the compositions and associated devices and apparatus can be used for on-body measurements of biofluids. Thus, lipoproteins can be monitored in several biofluids such as, for example, tears, saliva or sweat for non-invasive diagnosis in addition to the analysis of blood, blood plasma, extracellular fluid, urine, and the like. When the analyzed biofluid is sweat, the devices and apparatus can be used for long term and continuous monitoring of lipoproteins present in the sweat.

In certain embodiments, this invention relates to a composition comprising a specific probe molecule for the functionalization of sensors. The sensors can include, for example, an FET gate (e.g., a metallic or dielectric gate), an extended FET gate or an electrode surface. The probe molecule can include a low density lipoprotein receptor or a protein or amino acid sequence mimicking a recognition site or binding site of such a receptor. For example, for the sensing of LDL the probe molecule is selected to complex/bind/coordinate specifically the apolipoprotein B100 and/or the complex apolipoprotein B100/cholesterol and thus to determine the concentration of LDL in biofluids.

Disposing Receptor-Functionalized Compositions on a Sensor Surface

A receptor is a protein molecule of the cell membrane, the cytoplasm, or the cell nucleus that binds to a specific ligand inducing physiological modifications to the cell or cellular environment. Ligands can be, for example, proteins or peptides, or other small molecules (e.g., a hormone, a toxin, a neurotransmitter).

Figure 9:
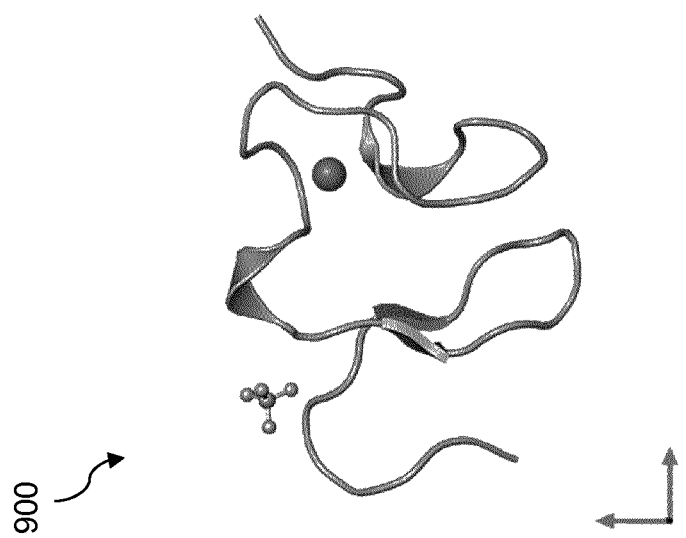
FIG. 9 is an illustration of an LDL receptor (LDL-R) binding a ligand.

The low density lipoprotein (LDL) receptor (LDL-R) is a cell surface receptor that recognizes (e.g., binds to) the apolipoprotein B100 present in the outer phospholipid layer of LDL particles and belongs to the low density receptor gene family. FIG. 9 shows an illustration 900 representing an LDL-R. LDL-R is a mosaic protein composed of 839 amino acids that mediates the active transport (endocytosis) of cholesterol-rich LDL.

Figure 10:
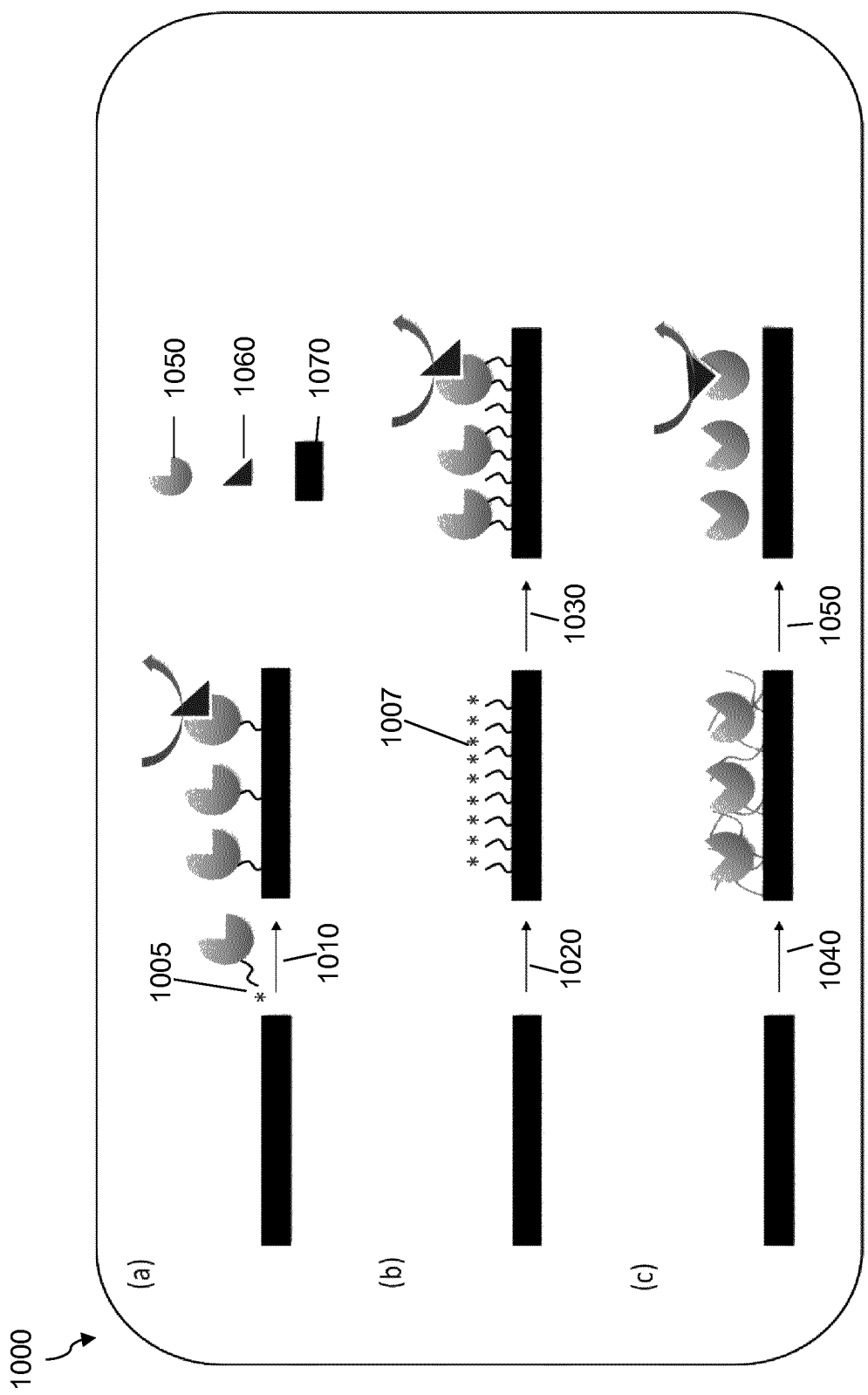
FIG. 10 is a schematic diagram of methods for disposing a receptor on a sensor surface, according to an illustrative embodiment.

A receptor, such as LDL-R, can be obtained from cellular samples (e.g., via extraction and separation processes) and disposed (e.g., immobilized) on the surface of sensor (e.g., the surface of the gate of an FET or the surface of an electrode). FIG. 10 shows an illustrative example 1000 of methods for disposing a receptor molecule 1050 on a surface of sensor 1070. Receptor molecule 1050 are coupled (Step 1010) to the sensor surface 1070 via functional group 1005 to form a monolayer. For example, functional group 1005 can be a thiol functional group. A thiol-functionalized receptor can be self-assembled on a metallic (e.g., Au) surface (e.g., via gold-thiol binding). The surface-bound receptor molecule can then bind with a ligand 1060 (e.g., a molecule of interest, e.g., a target analyte) to sense the ligand 1060.

In certain embodiments, the sensor surface 1070 is functionalized (Step 1020) with carbon chains that include a functional group 1007 (e.g., typically at or near a terminal end of the chain) that will bind to the receptor molecules 1050. For example, functional group 1007 can be a carboxy group. The receptor molecule 1050 (e.g., LDL-R) is then coupled (Step 1030) to the sensor surface 1070 (e.g., via peptidic coupling of the receptor to the carboxy functional groups 1007 on the sensor surface). The surface-bound receptor can then bind with a ligand 1060 (e.g., a molecule of interest, e.g., a target analyte) to sense the ligand 1060.

In certain embodiments, a matrix material is used to dispose the receptor molecule 1050 on the sensor surface 1070. The receptor molecule 1050 can, for example, be attached to the sensor surface 1070 by trapping receptor molecule 1050 in a polymer matrix disposed on the surface of the sensor. A receptor molecule 1050 and polymer matrix precursor are disposed on the sensor surface (Step 1040), and the polymer matrix precursor is subsequently polymerized (Step 1050). Polymerization of the polymer matrix precursor can be performed using the same or similar methods to those described above with respect to preparing a polymer membrane and an MIP membrane. The receptor molecule 1050 can bind (e.g., chemically and/or physically) to a polymer network (e.g., a photopolymerizable polyethylene glycol acrylate functionalized polymer network). The receptor molecule 1050 can bind to specific functional group in or on the polymer matrix. The receptor can also be physically trapped (e.g., embedded) in the polymer matrix by forming the polymer matrix in the presence of the receptor.

Once the receptor is dispose on the sensor surface, this sensor is sensitive to the presence of the molecule that the receptor binds to specifically. For example, a sensor with a sensing surface that includes LDL-R is sensitive to the presence and/or quantity of LDL in a fluid that is in contact with the surface. For example, the coordination or complexation of the receptor with the targeted ligand (LDL) leads to changes in the electronic environment of the sensor surface which can be monitored through for example open circuit potential or impedance measurements. Changes in these electronic signals can be correlated to LDL concentration.

Disposing Aptamer-Functionalized Compositions on a Sensor Surface

The sensor surface (e.g., a gate or extended gate of an FET, an electrode surface) can also or alternatively be functionalized with aptamers (e.g., instead of receptor(s) and/or MIP membranes(s)). As used herein, an aptamer is an oligonucleotide molecule with a known (e.g., engineered) sequence (e.g., a DNA or RNA molecule with a known nucleotide sequence) or a peptide molecule that preferentially binds to a given target molecule (e.g., a peptide molecule with a known affinity for a given target molecule). An aptamer can be used as a probe that binds selectively (e.g., and reversibly) with a specific target molecule. For example, the target molecule may be an oligonucleotide or peptide molecule with a nucleotide sequence that is complementary to that of the aptamer probe. For example, a target peptide molecule may hybridize, thus enabling a label-free detection. For example, an aptamer may selectively (e.g., and reversibly) bind with a variety of molecular targets including small molecules, proteins, peptides, and nucleic acids.

Aptamers can be immobilized on the metallic gate or extended metallic gate of an FET to selectively detect an analyte of interest (e.g., a target analyte). An FET that includes immobilized aptamers can be used as a biosensor to detect target analytes with a high specificity through the design and functionalization of the metallic gate (e.g., or extended metallic gate) of the FET, which acts as a transduction surface.

In certain embodiments, an FET biosensor includes aptamers that are immobilized on the gate or extended gate of an FET for the selective detection of low-density lipoprotein cholesterol (LDL-Ch) in a liquid sample. For the selective detection of LDL-Ch, the aptamers include nucleotide sequences related to the low-density lipoprotein (LDL) receptors in human cells. These receptors specifically target low-density lipoprotein cholesterol. Examples of such sequences include 5'-TCTGTCTCGAGGGGTAGCTG-3' (SEQ ID NO.1), 5'-CAATGTCTCACCAAGCTCTG-3' (SEQ ID NO.2), and 5'-ACCTCGATTTTATATTAT-TTCGCTTACCAACAACTGCAGA-3' (SEQ ID NO.3). These or other aptamer sequences may be selected to reproduce or mimic a specific complementary binding site of lipoprotein B1 in order to bind with a targeted protein. In an analogous manner, an aptamer sequence corresponding to and/or compatible with the apolipoprotein A can be used to specifically bind HDL particles for the detection and/or quantification of HDL. It should be understood to one of ordinary skill in the art that related or alternative aptamers (e.g., related or alternative nucleotide sequences) can be used in the systems, methods, devices, and architectures described herein, for example, when the related or alternative aptamer is known to bind to the target molecule (e.g., LDL).

In certain embodiments, the aptamer sequence includes an electrochemically active redox reporter (e.g., methylene blue) in order to facilitate electrochemical detection of binding between the aptamers and target molecules by operating the metallic surface of the gate or extended gate of an FET as a working electrode. For example, a redox reporter molecule may be more likely to come into contact with the working electrode and undergo electron transfer reactions before a target analyte molecule binds to the corresponding aptamer. After binding with the target analyte molecule, the target analyte molecule effectively blocks the redox reporter from accessing the electrode surface, and the redox reporter molecule is less likely to interact with (e.g., come sufficiently near) the electrode surface. The electrochemical activity—and by extension the measured current at the surface of the metallic gate or extended gate of the FET—of the reporter may thus vary as a function of the aptamer-target binding rate, allowing for an electronic readout of aptamer-target binding for the selective detection and/or quantitation of analyte molecules.

In other embodiments, an electrochemically active redox reporter is not required for the detection of the binding of aptamers and target molecules. For example, an FET biosensor may not require the aptamer to include an electrochemically active redox reporter. Instead of relying on direct electrochemical detection of aptamer-target binding, the FET biosensor indirectly measures binding of aptamers with target analytes. For example, the electrical resistance [e.g., measured as a current or voltage (e.g., a drain current or drain voltage)] of the FET may change as a function of the aptamer-target binding rate.

The aptamer is usually immobilized on the surface of the FET gate with a given concentration via the concentration of aptamers added to a functionalization solution with which the sensor is contacted and the amount of time this contact occurs.

In order to immobilize the aptamer on the metallic gate of a FET sensor made with gold (or other noble metals such as platinum), the aptamer sequence may be terminated (at the extremities) with thiol groups that will bind with the gold gate of each FET sensor via gold-thiol interactions/binding.

In order to immobilize the aptamer on the gate dielectric of a FET sensor (without metallic gate) made with an oxide (e.g. silicon dioxide, hafnium dioxide), the aptamer sequence may be terminated (at the extremities) with silane groups that will bind with the gate oxide of each FET sensor via silane-hydroxyl group interactions.

Example Network and Computer Implementation

Figure 11:
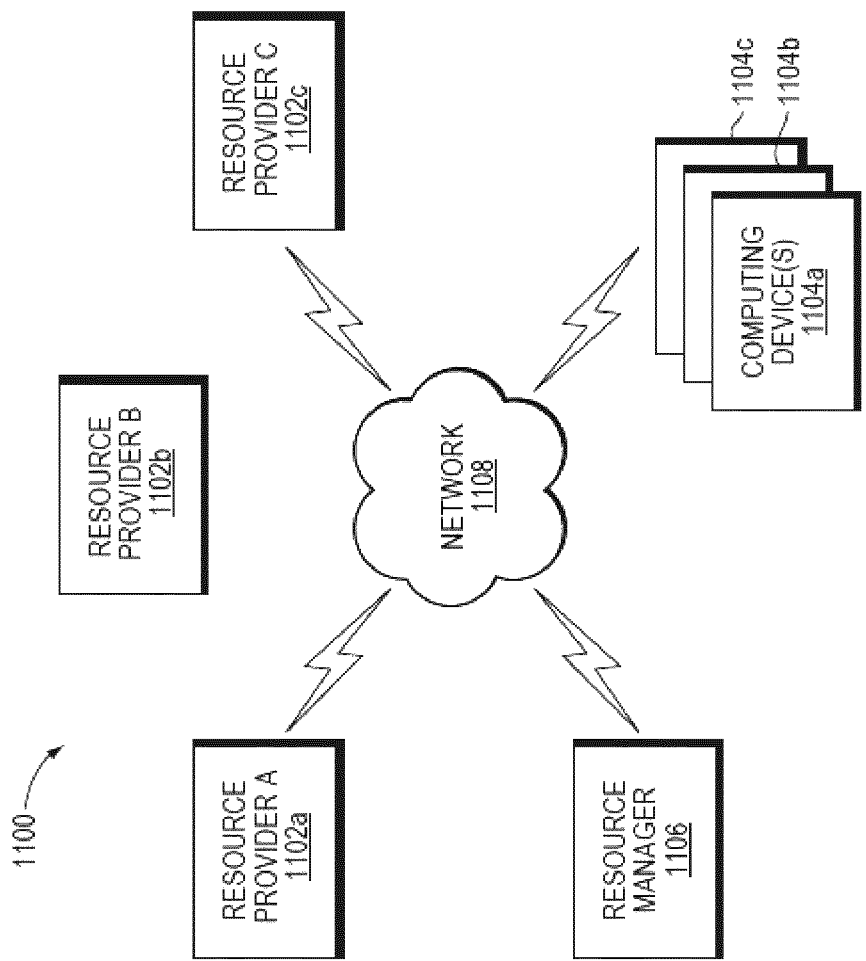
FIG. 11 is a block diagram of an example network environment for use in the methods and systems described herein, according to an illustrative embodiment.

As shown in FIG. 11, an implementation of a network environment 1100 for use in the systems, methods, and architectures described herein, is shown and described. In brief overview, referring now to FIG. 11, a block diagram of an exemplary cloud computing environment 1100 is shown and described. The cloud computing environment 1100 may include one or more resource providers 1102a, 1102b, 1102c (collectively, 1102). Each resource provider 1102 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1102 may be connected to any other resource provider 1102 in the cloud computing environment 1100. In some implementations, the resource providers 1102 may be connected over a computer network 1108. Each resource provider 1102 may be connected to one or more computing device 1104a, 1104b, 1104c (collectively, 1104), over the computer network 1108.

The cloud computing environment 1100 may include a resource manager 1106. The resource manager 1106 may be connected to the resource providers 1102 and the computing devices 1104 over the computer network 1108. In some implementations, the resource manager 1106 may facilitate the provision of computing resources by one or more resource providers 1102 to one or more computing devices 1104. The resource manager 1106 may receive a request for a computing resource from a particular computing device 1104. The resource manager 1106 may identify one or more resource providers 1102 capable of providing the computing resource requested by the computing device 1104. The resource manager 1106 may select a resource provider 1102 to provide the computing resource. The resource manager 1106 may facilitate a connection between the resource provider 1102 and a particular computing device 1104. In some implementations, the resource manager 1106 may establish a connection between a particular resource provider 1102 and a particular computing device 604. In some implementations, the resource manager 1106 may redirect a particular computing device 1104 to a particular resource provider 1102 with the requested computing resource.

Figure 12:
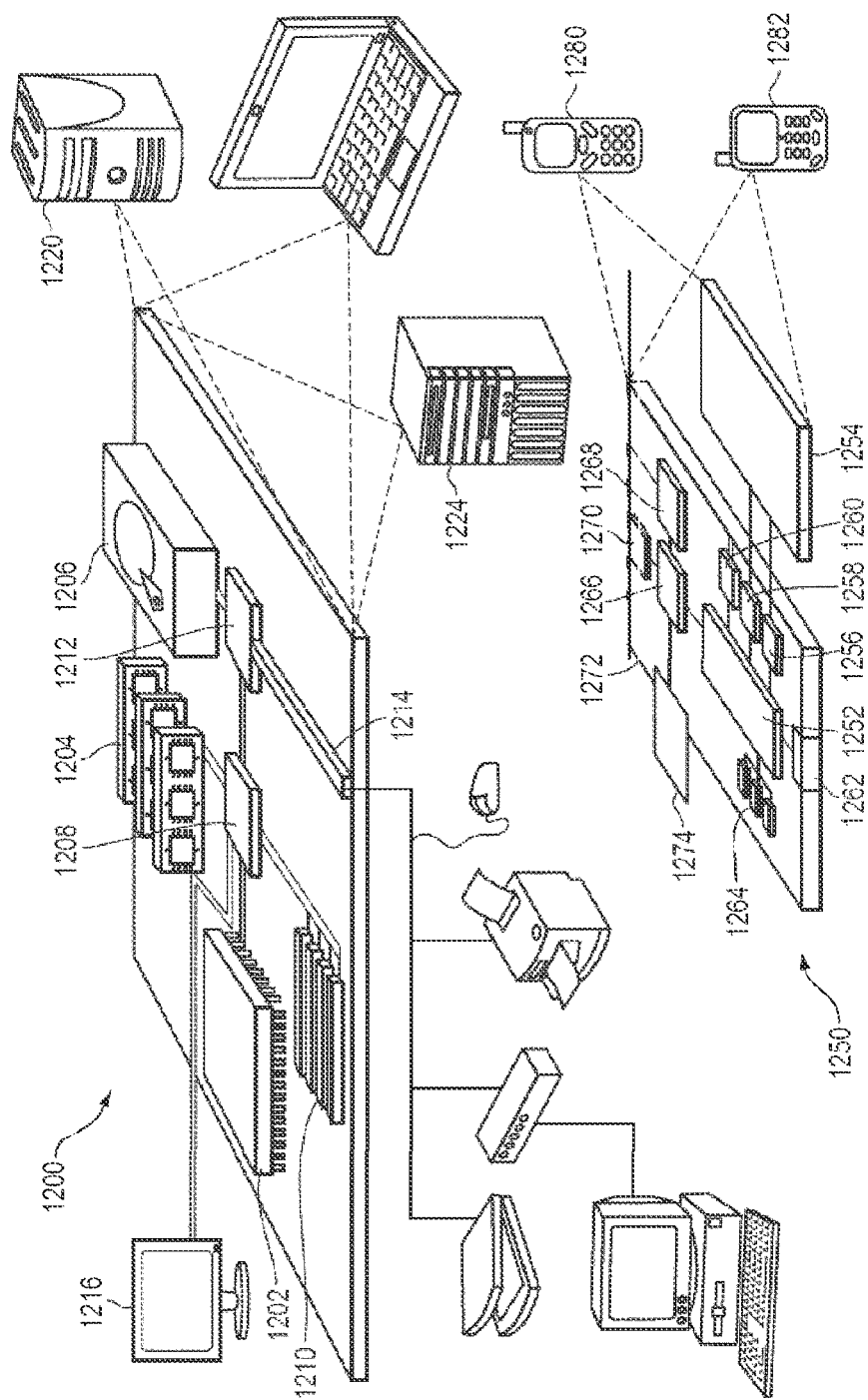
FIG. 12 is a block diagram of an example computing device and an example mobile computing device, for use in illustrative embodiments of the invention.

FIG. 12 shows an example of a computing device 1200 and a mobile computing device 1250 that can be used in the methods and systems described in this disclosure. The computing device 1200 is intended to represent various forms of digital computers, such as laptops, desktops, workstations, personal digital assistants, servers, blade servers, mainframes, and other appropriate computers. The mobile computing device 1250 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1200 includes a processor 1202, a memory 1204, a storage device 1206, a high-speed interface 1208 connecting to the memory 1204 and multiple high-speed expansion ports 1210, and a low-speed interface 1212 connecting to a low-speed expansion port 1214 and the storage device 1206. Each of the processor 1202, the memory 1204, the storage device 1206, the high-speed interface 1208, the high-speed expansion ports 1210, and the low-speed interface 1212, are interconnected using various busses, and may be mounted on a common motherboard or in other manners as appropriate. The processor 1202 can process instructions for execution within the computing device 1200, including instructions stored in the memory 1204 or on the storage device 1206 to display graphical information for a GUI on an external input/output device, such as a display 1216 coupled to the high-speed interface 1208. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 1204 stores information within the computing device 1200. In some implementations, the memory 1204 is a volatile memory unit or units. In some implementations, the memory 1204 is a non-volatile memory unit or units. The memory 1204 may also be another form of computer-readable medium, such as a magnetic or optical disk.

The storage device 1206 is capable of providing mass storage for the computing device 1200. In some implementations, the storage device 1206 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1202), perform one or more methods, such as those described above. The instructions can also be stored by one or more storage devices such as computer- or machine-readable mediums (for example, the memory 1204, the storage device 1206, or memory on the processor 1202).

The high-speed interface 1208 manages bandwidth-intensive operations for the computing device 1200, while the low-speed interface 1212 manages lower bandwidth-intensive operations. Such allocation of functions is an example only. In some implementations, the high-speed interface 1208 is coupled to the memory 1204, the display 1216 (e.g., through a graphics processor or accelerator), and to the high-speed expansion ports 1210, which may accept various expansion cards (not shown). In the implementation, the low-speed interface 1212 is coupled to the storage device 1206 and the low-speed expansion port 1214. The low-speed expansion port 1214, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1200 may be implemented in a number of different forms, as shown in the figure. For example, it may be implemented as a standard server 1220, or multiple times in a group of such servers. In addition, it may be implemented in a personal computer such as a laptop computer 1222. It may also be implemented as part of a rack server system 1224. Alternatively, components from the computing device 1200 may be combined with other components in a mobile device (not shown), such as a mobile computing device 1250. Each of such devices may contain one or more of the computing device 1200 and the mobile computing device 1250, and an entire system may be made up of multiple computing devices communicating with each other.

The mobile computing device 1250 includes a processor 1252, a memory 1264, an input/output device such as a display 1254, a communication interface 1266, and a transceiver 1268, among other components. The mobile computing device 1250 may also be provided with a storage device, such as a micro-drive or other device, to provide additional storage. Each of the processor 1252, the memory 1264, the display 1254, the communication interface 1266, and the transceiver 1268, are interconnected using various buses, and several of the components may be mounted on a common motherboard or in other manners as appropriate.

The processor 1252 can execute instructions within the mobile computing device 1250, including instructions stored in the memory 1264. The processor 1252 may be implemented as a chipset of chips that include separate and multiple analog and digital processors. The processor 1252 may provide, for example, for coordination of the other components of the mobile computing device 1250, such as control of user interfaces, applications run by the mobile computing device 1250, and wireless communication by the mobile computing device 1250.

The processor 1252 may communicate with a user through a control interface 1258 and a display interface 1256 coupled to the display 1254. The display 1254 may be, for example, a TFT (Thin-Film-Transistor Liquid Crystal Display) display or an OLED (Organic Light Emitting Diode) display, or other appropriate display technology. The display interface 1256 may comprise appropriate circuitry for driving the display 1254 to present graphical and other information to a user. The control interface 1258 may receive commands from a user and convert them for submission to the processor 1252. In addition, an external interface 1262 may provide communication with the processor 1252, so as to enable near area communication of the mobile computing device 1250 with other devices. The external interface 1262 may provide, for example, for wired communication in some implementations, or for wireless communication in other implementations, and multiple interfaces may also be used.

The memory 1264 stores information within the mobile computing device 1250. The memory 1264 can be implemented as one or more of a computer-readable medium or media, a volatile memory unit or units, or a non-volatile memory unit or units. An expansion memory 1274 may also be provided and connected to the mobile computing device 1250 through an expansion interface 1272, which may include, for example, a SIMM (Single In Line Memory Module) card interface or a DIMM (Double In Line Memory Module) card interface. The expansion memory 1274 may provide extra storage space for the mobile computing device 1250, or may also store applications or other information for the mobile computing device 1250. Specifically, the expansion memory 1274 may include instructions to carry out or supplement the processes described above, and may include secure information also. Thus, for example, the expansion memory 1274 may be provided as a security module for the mobile computing device 1250, and may be programmed with instructions that permit secure use of the mobile computing device 1250. In addition, secure applications may be provided via the DIMM cards, along with additional information, such as placing identifying information on the DIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 1252), perform one or more methods, such as those described above. The instructions can also be stored by one or more storage devices, such as one or more computer- or machine-readable mediums (for example, the memory 1264, the expansion memory 1274, or memory on the processor 1252). In some implementations, the instructions can be received in a propagated signal, for example, over the transceiver 1268 or the external interface 1262.

The mobile computing device 1250 may communicate wirelessly through the communication interface 1266, which may include digital signal processing circuitry where necessary. The communication interface 1266 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1268 using a radio-frequency. In addition, short-range communication may occur, such as using a Bluetooth®, Wi-Fi™, or other such transceiver (not shown). In addition, a GPS (Global Positioning System) receiver module 1270 may provide additional navigation- and location-related wireless data to the mobile computing device 1250, which may be used as appropriate by applications running on the mobile computing device 1250.

The mobile computing device 1250 may also communicate audibly using an audio codec 1260, which may receive spoken information from a user and convert it to usable digital information. The audio codec 1260 may likewise generate audible sound for a user, such as through a speaker, e.g., in a handset of the mobile computing device 1250. Such sound may include sound from voice telephone calls, may include recorded sound (e.g., voice messages, music files, etc.) and may also include sound generated by applications operating on the mobile computing device 1250.

The mobile computing device 1250 may be implemented in a number of different forms, as shown in the figure. For example, it may be implemented as a cellular telephone 1280. It may also be implemented as part of a smart-phone 1282, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the modules (e.g. data aggregation module 1230, mapping module 1250, specifications module 1270) described herein can be separated, combined or incorporated into single or combined modules. The modules depicted in the figures are not intended to limit the systems described herein to the software architectures shown therein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein. In view of the structure, functions and apparatus of the systems and methods described here, in some implementations.

The various described embodiments of the invention may be used in conjunction with one or more other embodiments unless technically incompatible.

While the invention has been particularly shown and described with reference to specific preferred embodiments, it should be understood by those skilled in the art that various changes in form and detail may be made therein without departing from the spirit and scope of the invention as defined by the appended claims.

The invention claimed is:

1. An apparatus for detecting and/or monitoring one or more molecules of interest in a biofluid, the apparatus comprising:
    a field-effect transistor disposed on and/or within a substrate, the field-effect transistor comprising one or more metallic gates; and
    one or more compositions for selectively sensing at least one of the one or more molecules of interest, wherein:
    the one or more compositions comprise a molecularly imprinted polymer (MIP) membrane, and
    each of the one or more compositions is disposed on at least a portion of a surface of at least one of the one or more metallic gates, wherein the MIP membrane comprises (i) a plurality of cavities that are shaped and sized to selectively bind to the one or more molecules of interest and (ii) one or more materials selected from the group consisting of polyvinyl chloride, polystyrene, poly-(3-aminophenylboronic acid) and derivative, polyaniline and derivative, polysiloxane and derivative, polypyrrole, and poly (3,4-ethylenedioxythiophene).

2. The apparatus of claim 1, wherein the biofluid comprises a member selected from the group consisting of sweat, tears, saliva, urine, blood, blood plasma, and extracellular fluid.

3. The apparatus of claim 1, wherein the field-effect transistor is a fully depleted field-effect transistor or a Fin FET.

4. The apparatus of claim 1, wherein at least one of the one or more metallic gates is an extended metallic gate.

5. The apparatus of claim 1, wherein the molecularly imprinted polymer (MIP) membrane has a thickness in a range from about 1 nm to about 100 μm.

6. The apparatus of claim 1, wherein the molecularly imprinted polymer (MIP) membrane is disposed on 50% or more of the surface of the at least one of the one or more metallic gates.

7. The apparatus of claim 1, wherein the molecularly imprinted polymer membrane has been prepared via electro-polymerization, photo-polymerization, deposition, or via polymerization.

8. The apparatus of claim 1, comprising:
an interface, the interface comprising at least one biocompatible material for contacting a body part,
at least one inlet for receiving the biofluid,
at least one outlet for evacuating the biofluid, and
at least one microfluidic and/or nanofluidic channel in fluid communication with the at least one inlet, wherein at least one of the one or more compositions is disposed on the at least one of the one or more metallic gates of the field-effect transistor, and the at least one outlet.

9. The apparatus of claim 8, wherein the at least one microfluidic and/or nanofluidic channel has an internal volume in a range from about 0.1 nL to about 10 μL.

10. The apparatus of claim 8, further comprising an electronic circuit operably connected to the field-effect transistor, wherein the electronic circuit produces and/or measures and/or transmits signals representative of measured data from the field-effect transistor corresponding to a presence and/or amount of at least one of the one or more molecules of interest.

11. The apparatus of claim 10, comprising a wireless communication element for transmitting data and/or signals measured and/or calculated by the electronic circuit to an external device.

12. The apparatus of claim 1, wherein the biofluid is not processed prior to detecting and/or monitoring the one or more molecules of interest in the biofluid.

13. The apparatus of claim 1, wherein the one or more molecules of interest are detected and/or monitored in the biofluid continuously and/or for an extended period of time.

14. The apparatus of claim 1, wherein the one or more compositions further comprise one or more probe materials.

15. A method of manufacturing a molecularly imprinted polymer membrane, the method comprising:
contacting a template species with one or more monomers on or near a surface of a metallic gate of a field-effect transistor;
exposing the one or more monomers to a crosslinking agent and/or performing a crosslinking step for the one or more monomers to produce a polymer membrane, said polymer membrane comprising bound template species and one or more materials selected from the group consisting of polyvinyl chloride, polystyrene, poly-(3-aminophenylboronic acid) and derivative, polyaniline and derivative, polysiloxane and derivative, polypyrrole, and poly(3,4-ethylenedioxythiophene); and
removing at least a portion of the bound template species from the polymer membrane to produce the molecularly imprinted polymer membrane, wherein the molecularly imprinted polymer membrane comprises a plurality of cavities that are shaped and sized to selectively bind to one or more molecules of interest.

16. The method of claim 15, wherein the one or more monomers comprise a member selected from the group consisting of: an electrochemically polymerizable monomer, a photocurable monomer, and a chemically polymerizable monomer.

17. The method of claim 15, comprising the step of performing the crosslinking step for the one or more monomers, wherein performing the crosslinking step comprises:
contacting a metallic gate of a field-effect transistor with the one or more monomers; and
applying a potential or a current to the metallic gate of the field-effect transistor to produce the molecularly imprinted polymer membrane.

* * * * *